(12) United States Patent
Moller et al.

(10) Patent No.: US 12,729,398 B2
(45) **Date of Patent: *Sep. 8, 2026**

(54) CIRCULATING SERUM MICRORNA BIOMARKERS AND METHODS

(71) Applicant: ST. JOHN'S UNIVERSITY, Queens, NY (US)

(72) Inventors: Simon Geir Moller, Queens, NY (US); Indranil Basak, Queens, NY (US); Ketan Patil, Queens, NY (US); Jan Petter Larsen, Queens, NY (US)

(73) Assignee: ST. JOHN'S UNIVERSITY, Queens, NY (US)

( * ) Notice: Subject to any disclaimer, the term of this patent is extended or adjusted under 35 U.S.C. 154(b) by 817 days.

This patent is subject to a terminal disclaimer.

(21) Appl. No.: 18/045,065

(22) Filed: Oct. 7, 2022

(65) Prior Publication Data

US 2023/0323442 A1 Oct. 12, 2023

Related U.S. Application Data

(62) Division of application No. 16/075,354, filed as application No. PCT/US2017/016412 on Feb. 3, 2017, now Pat. No. 11,499,184.

(60) Provisional application No. 62/291,619, filed on Feb. 5, 2016.

(51) Int. Cl.
*C12Q 1/686* (2018.01)
*C12Q 1/6883* (2018.01)

(52) U.S. Cl.
CPC ........... *C12Q 1/686* (2013.01); *C12Q 1/6883* (2013.01); *C12Q 2600/158* (2013.01); *C12Q 2600/178* (2013.01)

(58) Field of Classification Search
CPC .................. C12Q 1/686; C12Q 1/6883; C12Q 2600/158; C12Q 2600/178
See application file for complete search history.

(56) References Cited

U.S. PATENT DOCUMENTS

2015/0197809 A1* 7/2015 Myers .................. C12Q 1/6883 435/6.12
2015/0275299 A1 10/2015 Xu

FOREIGN PATENT DOCUMENTS

WO 2013/036936 A1 3/2013
WO 2014/018650 A1 1/2014
WO 2014/075822 A1 5/2014
WO WO-2014179765 A2 * 11/2014 ........... C12Q 1/6886
WO 2015/091892 A1 6/2015

OTHER PUBLICATIONS

Saint Louis University, Analysis of RNA-Seq Data with Partek® Genomics Suite™ 6.6, [online]. Saint Louis University, [2012][retrieved on Oct. 22, 2025]. Retrieved from: https://biochem.slu.edu/bchm628/handouts/2015/PGS_RNASeqTutorial.pdf (Year: 2012).*

(Continued)

*Primary Examiner* — Anne M. Gussow
*Assistant Examiner* — Allison E Schloop
(74) *Attorney, Agent, or Firm* — VENABLE LLP

(57) ABSTRACT

Biomarkers and methods for identifying, verifying and confirming circulating serum-based microRNAs. The microRNAs (PARKmiRs) can be used to differentiate patient's suffering from Parkinson's disease (PD) from non-PD patients.

34 Claims, 18 Drawing Sheets

Specification includes a Sequence Listing.

(56) References Cited

OTHER PUBLICATIONS

JMP, Normal Distribution, [online]. JMP Statistical Discovery, [2025] [retrieved on Oct. 22, 2025]. Retrieved from: http://jmp.com/en/statistics-knowledge-portal/measures-of-central-tendency-and-variability/normal-distribution (Year: 2025).*
Acharya et al., Non-Coding RNAs in the Brain-Heart Axis: The case of Parkinson's Disease, Int. J. Mol. Sci., vol. 21, 6513, pp. 1-27 (2020).
Alvarez-Erviti et al., "Lysosomal dysfunction increases exosome-mediated alpha synuclein release and transmission" Neurobiology of Disease, vol. 42 (2011) 360 67.
Bartel, "MicroRNAs: Genomics, Biogenesis, Mechanism, and Function", Cell, vol. 116 (2004) 281-97.
Botta-Orfila, Teresa, Identification of Blood Serum Micro-RNAs Associated With Idiopathic and LRRK2 Parkinson's Disease, Journal of Neuroscience Research, vol. 92 (2014) 1071-77.
Burgos, et al., "Profiles of Extracellular miRNA in Cerebrospinal Fluid and Serum from Patients with Alzheimer's and Parkinson's Diseases Correlate with Disease Status and Features of Pathology", PLOS One, vol. 9, No. 5 (2014) 94839.
Burgos et al., PLOS One, vol. 9, e94839, supplemental material pp. 1-13 (2014).
Cathew, et al., "Origins and Mechanisms of miRNAs and siRNAs", Cell, vol. 136, No. 4 (2009) 642-55.
Chen et al., "Characterization of microRNAs in serum: a novel class of biomarkers for diagnosis of cancer and other diseases", Cell Research, vol. 18 (2008) 997-1006.
De Planell-Saguer et al., "Detection methods for microRNAs in clinic practice," Clinical Biochemistry 46 (2013) pp. 869-878.
Drahl, "Antibodies Against RNA" Biological Chemistry, vol. 85, Issue 52, Dec. 24, 2007.
Grasso et al., "Circulating miRNAs as Biomarkers for Neurodegenerative Disorders", Molecules, vol. 19 (2014) 6891-910.
Gregory et al., "The Microprocessor complex mediates the genesis of microRNAs", Nature, vol. 432 (2004) 235-40.
Han et al., "The Drosha—DGCR8 complex in primary microRNA processing", Genes & Development, vol. 18 (2004) 3016-20.
Hunt et al., MicroRNA Detection: Current Technology and Research Strategies, Annu. Rev. Anal. Chem., vol. 8, pp. 217-237 (2015).
Kim et al., "Biogenesis of small RNAs in animals", Nature, vol. 126 (2009) 126-39.
Koval et al., "Method for widespread microRNA-155 inhibition prolongs survival in ALS-model mice", Human Molecular Genetics, vol. 22, No. 20 (2013) 4127-35.
Lee et al., "The nuclear RNase III Drosha initiates microRNA processing", Nature, vol. 425 (2003) 415-19.
Leshkovitz et al., Differences in microRNA detection levels are technology and sequence dependent, RNA, vol. 19, pp. 527-538 (2013).
Macrae et al., "In vitro reconstitution of the human RISC-loading complex", PNAS, vol. 105, No. 2 (2008) 512-17.
Parikh, et al., "Analysis of MicroRNA Niches: Techniques to Measure Extracellular MicroRNA and Intracellular MicroRNA In Situ" NIH Public Access, Methods Mol. Biol. 2013; 1024: 157-172.
Saghazadeh, et al., "MicroRNA machinery in Parkinson's disease: a platform for neurodegenerative diseases", Expert Rev. Eurother. (2015) 1-27.
Shinde, et al., "Biofluid-based microRNA Biomarkers for Parkinson's Disease: an Overview and Update" vol. 2, Issue 1 (2015) 15-25.
Siomi et al., "Posttranscriptional Regulation of MicroRNA Biogenesis in Animals" Molecular Cell, vol. 38 (2010) 323-32.
Tran et al., "Antibodies Directed to RNA/DNA Hybrids: An Electrochemical Immunosensor for MicroRNAs Detection using Graphene-Composite Electrodes," American Chemical Society 2013, 85, pp. 8469-8474.
Zhang et al., Simultaneous and ultrasensitive detection of multiple microRNAs by single-molecule florescence imaging, Royal Society of Chemistry 2020, pp. 3812-3819.
Affymetrix GeneChip® miRNA 4.0 Array by the Yale Center for Genome Analysis (http://medicine.yale.edu/keck/ycga/index.aspx).

* cited by examiner

SEQUENCE LISTING

```
Sequence total quantity: 88
SEQ ID NO: 1            moltype = RNA  length = 22
FEATURE                 Location/Qualifiers
source                  1..22
                        mol_type = unassigned RNA
                        organism = Homo sapiens
SEQUENCE: 1
tcaccgggtg taaatcagct tg                                           22

SEQ ID NO: 2            moltype = RNA  length = 79
FEATURE                 Location/Qualifiers
source                  1..79
                        mol_type = unassigned RNA
                        organism = Homo sapiens
SEQUENCE: 2
cccgggctga ggtaggaggt tgtatagttg aggaggacac ccaaggagat cactatacgg  60
cctcctagct ttccccagg                                               79

SEQ ID NO: 3            moltype = RNA  length = 23
FEATURE                 Location/Qualifiers
source                  1..23
```

```
                        mol_type = unassigned RNA
                        organism = Homo sapiens
SEQUENCE: 3
cctgcagcga cttgatggct tcc                                             23

SEQ ID NO: 4            moltype = RNA  length = 111
FEATURE                 Location/Qualifiers
source                  1..111
                        mol_type = unassigned RNA
                        organism = Homo sapiens
SEQUENCE: 4
ccacggtcct agttaaaaag gcacattcct agaccctgcc tcagaactac tgaacagagt  60
cactgggtgt ggagtccagg aatctgcatt tttacccta tcgcccccgc c            111

SEQ ID NO: 5            moltype = RNA  length = 22
FEATURE                 Location/Qualifiers
source                  1..22
                        mol_type = unassigned RNA
                        organism = Homo sapiens
SEQUENCE: 5
tcaaaactga ggggcatttt ct                                              22

SEQ ID NO: 6            moltype = RNA  length = 22
FEATURE                 Location/Qualifiers
source                  1..22
                        mol_type = unassigned RNA
                        organism = Homo sapiens
SEQUENCE: 6
gctatttcac gacaccaggg tt                                              22

SEQ ID NO: 7            moltype = RNA  length = 22
FEATURE                 Location/Qualifiers
source                  1..22
                        mol_type = unassigned RNA
                        organism = Homo sapiens
SEQUENCE: 7
ctcctacata ttagcattaa ca                                              22

SEQ ID NO: 8            moltype = RNA  length = 22
FEATURE                 Location/Qualifiers
source                  1..22
                        mol_type = unassigned RNA
                        organism = Homo sapiens
SEQUENCE: 8
ccaatattac tgtgctgctt ta                                              22

SEQ ID NO: 9            moltype = RNA  length = 23
FEATURE                 Location/Qualifiers
source                  1..23
                        mol_type = unassigned RNA
                        organism = Homo sapiens
SEQUENCE: 9
aacattcatt gctgtcggtg ggt                                             23

SEQ ID NO: 10           moltype = RNA  length = 21
FEATURE                 Location/Qualifiers
source                  1..21
                        mol_type = unassigned RNA
                        organism = Homo sapiens
SEQUENCE: 10
ctatatatca aacatattcc t                                               21

SEQ ID NO: 11           moltype = RNA  length = 21
FEATURE                 Location/Qualifiers
source                  1..21
                        mol_type = unassigned RNA
                        organism = Homo sapiens
SEQUENCE: 11
atgacctatg aattgacaga c                                               21

SEQ ID NO: 12           moltype = RNA  length = 22
FEATURE                 Location/Qualifiers
source                  1..22
                        mol_type = unassigned RNA
                        organism = Homo sapiens
SEQUENCE: 12
acctggcata caatgtagat tt                                              22

SEQ ID NO: 13           moltype = RNA  length = 24
```

```
FEATURE                Location/Qualifiers
source                 1..24
                       mol_type = unassigned RNA
                       organism = Homo sapiens
SEQUENCE: 13
agcgcgggct gagcgctgcc agtc                                          24

SEQ ID NO: 14          moltype = RNA  length = 21
FEATURE                Location/Qualifiers
source                 1..21
                       mol_type = unassigned RNA
                       organism = Homo sapiens
SEQUENCE: 14
atccccagat acaatggaca a                                             21

SEQ ID NO: 15          moltype = RNA  length = 22
FEATURE                Location/Qualifiers
source                 1..22
                       mol_type = unassigned RNA
                       organism = Homo sapiens
SEQUENCE: 15
tggtttaccg tcccacatac at                                            22

SEQ ID NO: 16          moltype = RNA  length = 23
FEATURE                Location/Qualifiers
source                 1..23
                       mol_type = unassigned RNA
                       organism = Homo sapiens
SEQUENCE: 16
ctgactgaat aggtagggtc att                                           23

SEQ ID NO: 17          moltype = RNA  length = 86
FEATURE                Location/Qualifiers
source                 1..86
                       mol_type = unassigned RNA
                       organism = Homo sapiens
SEQUENCE: 17
gagggaaagc aggccaacct cgaggatctc cccagccttg gcgttcaggt gctgaggaga  60
tcgtcgaggt tggcctgctt cccctc                                        86

SEQ ID NO: 18          moltype = RNA  length = 85
FEATURE                Location/Qualifiers
source                 1..85
                       mol_type = unassigned RNA
                       organism = Homo sapiens
SEQUENCE: 18
ggacctgccc tgggctttct agtctcagct ctcctccagc tcagctggtc aggagagctg  60
agactagaaa gcccagggca ggttc                                         85

SEQ ID NO: 19          moltype = RNA  length = 81
FEATURE                Location/Qualifiers
source                 1..81
                       mol_type = unassigned RNA
                       organism = Homo sapiens
SEQUENCE: 19
acctgccctg ggctttctag tctcagctct cctgaccagc tgagctggag gagagctgag  60
actagaaagc ccagggcagg t                                             81

SEQ ID NO: 20          moltype = RNA  length = 85
FEATURE                Location/Qualifiers
source                 1..85
                       mol_type = unassigned RNA
                       organism = Homo sapiens
SEQUENCE: 20
ggcgcctcct gctctgctgt gccgccaggg cctcccctag cgcgccttct ggagaggctt  60
tgtgcggata cggggctgga ggcct                                         85

SEQ ID NO: 21          moltype = RNA  length = 79
FEATURE                Location/Qualifiers
source                 1..79
                       mol_type = unassigned RNA
                       organism = Homo sapiens
SEQUENCE: 21
aattaatccc tctctttcta gttcttccta gagtgaggaa aagctgggtt gagagggcaa  60
acaaattaac taattaatt                                                79

SEQ ID NO: 22          moltype = RNA  length = 23
FEATURE                Location/Qualifiers
source                 1..23
```

```
                         mol_type = unassigned RNA
                         organism = Homo sapiens
SEQUENCE: 22
tcaagagcaa taacgaaaaa tgt                                              23

SEQ ID NO: 23            moltype = RNA  length = 98
FEATURE                  Location/Qualifiers
source                   1..98
                         mol_type = unassigned RNA
                         organism = Homo sapiens
SEQUENCE: 23
acccaaaccc taggtctgct gactcctagt ccagggctcg tgatggctgg tgggccctga  60
acgaggggtc tggaggcctg ggtttgaata tcgacagc                              98

SEQ ID NO: 24            moltype = RNA  length = 23
FEATURE                  Location/Qualifiers
source                   1..23
                         mol_type = unassigned RNA
                         organism = Homo sapiens
SEQUENCE: 24
taggcagtgt cattagctga ttg                                              23

SEQ ID NO: 25            moltype = RNA  length = 24
FEATURE                  Location/Qualifiers
source                   1..24
                         mol_type = unassigned RNA
                         organism = Homo sapiens
SEQUENCE: 25
acaaaaaaaa aagcccaacc cttc                                             24

SEQ ID NO: 26            moltype = RNA  length = 92
FEATURE                  Location/Qualifiers
source                   1..92
                         mol_type = unassigned RNA
                         organism = Homo sapiens
SEQUENCE: 26
tgtcactccg ccagcatcat gaagtgcact catgatatgt ttgccccatc agcgtgtcac  60
gagggcattt catgatgcag gcggggttgg ca                                    92

SEQ ID NO: 27            moltype = RNA  length = 22
FEATURE                  Location/Qualifiers
source                   1..22
                         mol_type = unassigned RNA
                         organism = Homo sapiens
SEQUENCE: 27
ctgggaggtg tgatatcgtg gt                                               22

SEQ ID NO: 28            moltype = RNA  length = 19
FEATURE                  Location/Qualifiers
source                   1..19
                         mol_type = unassigned RNA
                         organism = Homo sapiens
SEQUENCE: 28
actggacttg gaggcagaa                                                   19

SEQ ID NO: 29            moltype = RNA  length = 111
FEATURE                  Location/Qualifiers
source                   1..111
                         mol_type = unassigned RNA
                         organism = Homo sapiens
SEQUENCE: 29
cttttgctgt cagtttttct gttgcttgtc ttggttttat gccttttata tcaaggcaca  60
taaaaggcat aaaaccaaga caagcaacaa aaaaaggatt gatcacagaa g               111

SEQ ID NO: 30            moltype = RNA  length = 22
FEATURE                  Location/Qualifiers
source                   1..22
                         mol_type = unassigned RNA
                         organism = Homo sapiens
SEQUENCE: 30
tcaggtgtgg aaactgaggc ag                                               22

SEQ ID NO: 31            moltype = RNA  length = 17
FEATURE                  Location/Qualifiers
source                   1..17
                         mol_type = unassigned RNA
                         organism = Homo sapiens
SEQUENCE: 31
tggagagaaa ggcagta                                                     17
```

```
SEQ ID NO: 32           moltype = RNA  length = 20
FEATURE                 Location/Qualifiers
source                  1..20
                        mol_type = unassigned RNA
                        organism = Homo sapiens
SEQUENCE: 32
agccccctgg ccccaaaccc                                              20

SEQ ID NO: 33           moltype = RNA  length = 18
FEATURE                 Location/Qualifiers
source                  1..18
                        mol_type = unassigned RNA
                        organism = Homo sapiens
SEQUENCE: 33
ttgcacttgt ctcagtga                                                18

SEQ ID NO: 34           moltype = RNA  length = 94
FEATURE                 Location/Qualifiers
source                  1..94
                        mol_type = unassigned RNA
                        organism = Homo sapiens
SEQUENCE: 34
tggtttgcga ctctgaaaac tagaaggttt atgactgggc atttctcacc caatgcccaa  60
tattgaactt tctagttgtc agagtcatta accc                              94

SEQ ID NO: 35           moltype = RNA  length = 70
FEATURE                 Location/Qualifiers
source                  1..70
                        mol_type = unassigned RNA
                        organism = Homo sapiens
SEQUENCE: 35
ttcctgcaga ttgtttcttt tgccgtgcaa gtttaagttt ttgcacggca aaagaaacaa  60
tccagagggt                                                         70

SEQ ID NO: 36           moltype = RNA  length = 73
FEATURE                 Location/Qualifiers
source                  1..73
                        mol_type = unassigned RNA
                        organism = Homo sapiens
SEQUENCE: 36
actgtccttc agccagagct ggctgaaggg cagaagggaa ctgtccttca gccagagctg  60
gctgaagggc aga                                                     73

SEQ ID NO: 37           moltype = RNA  length = 22
FEATURE                 Location/Qualifiers
source                  1..22
                        mol_type = unassigned RNA
                        organism = Homo sapiens
SEQUENCE: 37
ttttgcaata tgttcctgaa ta                                           22

SEQ ID NO: 38           moltype = RNA  length = 21
FEATURE                 Location/Qualifiers
source                  1..21
                        mol_type = unassigned RNA
                        organism = Homo sapiens
SEQUENCE: 38
gcagtccatg ggcatataca c                                            21

SEQ ID NO: 39           moltype = RNA  length = 81
FEATURE                 Location/Qualifiers
source                  1..81
                        mol_type = unassigned RNA
                        organism = Homo sapiens
SEQUENCE: 39
ggctgcttct cgcctctgtc cagctgtgtg gccttggaca agcctcttgg ttacacagct  60
ggacagaggc acgaaacagc c                                            81

SEQ ID NO: 40           moltype = RNA  length = 26
FEATURE                 Location/Qualifiers
source                  1..26
                        mol_type = unassigned RNA
                        organism = Homo sapiens
SEQUENCE: 40
cccagggctt ggagtggggc aaggtt                                       26

SEQ ID NO: 41           moltype = RNA  length = 22
FEATURE                 Location/Qualifiers
```

```
source                  1..22
                        mol_type = unassigned RNA
                        organism = Homo sapiens
SEQUENCE: 41
agcaaggcgg catctctctg at                                                22

SEQ ID NO: 42           moltype = RNA  length = 22
FEATURE                 Location/Qualifiers
source                  1..22
                        mol_type = unassigned RNA
                        organism = Homo sapiens
SEQUENCE: 42
tgcggggaca ggccagggca tc                                                22

SEQ ID NO: 43           moltype = RNA  length = 22
FEATURE                 Location/Qualifiers
source                  1..22
                        mol_type = unassigned RNA
                        organism = Homo sapiens
SEQUENCE: 43
tctgccatcc tccctcccct ac                                                22

SEQ ID NO: 44           moltype = RNA  length = 21
FEATURE                 Location/Qualifiers
source                  1..21
                        mol_type = unassigned RNA
                        organism = Homo sapiens
SEQUENCE: 44
agcagacttg acctacaatt a                                                 21

SEQ ID NO: 45           moltype = RNA  length = 80
FEATURE                 Location/Qualifiers
source                  1..80
                        mol_type = unassigned RNA
                        organism = Homo sapiens
SEQUENCE: 45
aatgaaggat tacggaccag ctaagggagg cattaggatc cttattcttg cctcccttag  60
ttggtcccta atccttcgtt                                                   80

SEQ ID NO: 46           moltype = RNA  length = 18
FEATURE                 Location/Qualifiers
source                  1..18
                        mol_type = unassigned RNA
                        organism = Homo sapiens
SEQUENCE: 46
tggatatgat gactgaaa                                                     18

SEQ ID NO: 47           moltype = RNA  length = 21
FEATURE                 Location/Qualifiers
source                  1..21
                        mol_type = unassigned RNA
                        organism = Homo sapiens
SEQUENCE: 47
gacagagtgc cacttactga a                                                 21

SEQ ID NO: 48           moltype = RNA  length = 22
FEATURE                 Location/Qualifiers
source                  1..22
                        mol_type = unassigned RNA
                        organism = Homo sapiens
SEQUENCE: 48
atgcacctgg gcaaggattc tg                                                22

SEQ ID NO: 49           moltype = RNA  length = 22
FEATURE                 Location/Qualifiers
source                  1..22
                        mol_type = unassigned RNA
                        organism = Homo sapiens
SEQUENCE: 49
tgattggtac gtctgtgggt ag                                                22

SEQ ID NO: 50           moltype = RNA  length = 22
FEATURE                 Location/Qualifiers
source                  1..22
                        mol_type = unassigned RNA
                        organism = Homo sapiens
SEQUENCE: 50
tactcaggag agtggcaatc ac                                                22
```

-continued

```
SEQ ID NO: 51          moltype = RNA  length = 21
FEATURE                Location/Qualifiers
source                 1..21
                       mol_type = unassigned RNA
                       organism = Homo sapiens
SEQUENCE: 51
ctccagaggg aagtactttc t                                         21

SEQ ID NO: 52          moltype = RNA  length = 90
FEATURE                Location/Qualifiers
source                 1..90
                       mol_type = unassigned RNA
                       organism = Homo sapiens
SEQUENCE: 52
tcccatgctg tgaccctcta gaggaagcac tttctgtttg ttgtctgaga aaaaacaaag  60
tgcttccctt tagagtgtta ccgtttggga                                90

SEQ ID NO: 53          moltype = RNA  length = 88
FEATURE                Location/Qualifiers
source                 1..88
                       mol_type = unassigned RNA
                       organism = Homo sapiens
SEQUENCE: 53
tcccatgctg tgaccctcta gaggaagcac tttctgtttg ttgtctgaga aaaaacaaag  60
tgcttccctt tagagttact gtttggga                                  88

SEQ ID NO: 54          moltype = RNA  length = 91
FEATURE                Location/Qualifiers
source                 1..91
                       mol_type = unassigned RNA
                       organism = Homo sapiens
SEQUENCE: 54
cgacttgctt tctctcctcc atgccttgag tgtaggaccg ttggcatctt aattaccctc  60
ccacacccaa ggcttgcaga agagcgagcc t                              91

SEQ ID NO: 55          moltype = RNA  length = 25
FEATURE                Location/Qualifiers
source                 1..25
                       mol_type = unassigned RNA
                       organism = Homo sapiens
SEQUENCE: 55
aaaaaccaca attacttttg cacca                                     25

SEQ ID NO: 56          moltype = RNA  length = 22
FEATURE                Location/Qualifiers
source                 1..22
                       mol_type = unassigned RNA
                       organism = Homo sapiens
SEQUENCE: 56
caaaaaccgg caattacttt tg                                        22

SEQ ID NO: 57          moltype = RNA  length = 21
FEATURE                Location/Qualifiers
source                 1..21
                       mol_type = unassigned RNA
                       organism = Homo sapiens
SEQUENCE: 57
caaaaactgc aattactttc a                                         21

SEQ ID NO: 58          moltype = RNA  length = 21
FEATURE                Location/Qualifiers
source                 1..21
                       mol_type = unassigned RNA
                       organism = Homo sapiens
SEQUENCE: 58
aaaggtaatt gtggtttctg c                                         21

SEQ ID NO: 59          moltype = RNA  length = 21
FEATURE                Location/Qualifiers
source                 1..21
                       mol_type = unassigned RNA
                       organism = Homo sapiens
SEQUENCE: 59
taaaaactgc aattactttt a                                         21

SEQ ID NO: 60          moltype = RNA  length = 19
FEATURE                Location/Qualifiers
source                 1..19
                       mol_type = unassigned RNA
```

```
                         organism = Homo sapiens
SEQUENCE: 60
aaaaaccaca attactttt                                           19

SEQ ID NO: 61            moltype = RNA  length = 54
FEATURE                  Location/Qualifiers
source                   1..54
                         mol_type = unassigned RNA
                         organism = Homo sapiens
SEQUENCE: 61
aaaagtaatt gcggttttg ctattggttt taatggcagt tacttttgca ccag     54

SEQ ID NO: 62            moltype = RNA  length = 22
FEATURE                  Location/Qualifiers
source                   1..22
                         mol_type = unassigned RNA
                         organism = Homo sapiens
SEQUENCE: 62
aaaagtactt gcggattttg ct                                       22

SEQ ID NO: 63            moltype = RNA  length = 25
FEATURE                  Location/Qualifiers
source                   1..25
                         mol_type = unassigned RNA
                         organism = Homo sapiens
SEQUENCE: 63
aaaaaccaca attacttttg cacca                                    25

SEQ ID NO: 64            moltype = RNA  length = 20
FEATURE                  Location/Qualifiers
source                   1..20
                         mol_type = unassigned RNA
                         organism = Homo sapiens
SEQUENCE: 64
taaaaactgc aattactttc                                          20

SEQ ID NO: 65            moltype = RNA  length = 110
FEATURE                  Location/Qualifiers
source                   1..110
                         mol_type = unassigned RNA
                         organism = Homo sapiens
SEQUENCE: 65
gcctaaacta ttaggttggt gcaaaagtaa tcactgtttt tgccattact ctcagtggca  60
aaaaccgtga ttacttttgc accaacctag taacaccttc actgtggggg             110

SEQ ID NO: 66            moltype = RNA  length = 97
FEATURE                  Location/Qualifiers
source                   1..97
                         mol_type = unassigned RNA
                         organism = Homo sapiens
SEQUENCE: 66
cttcatccac cagtcctcca ggaacatcaa ggatcttaaa ctttgccaga gctacaaagg  60
caaagtttaa gatccttgaa gttcctgggg gaaccat                           97

SEQ ID NO: 67            moltype = RNA  length = 22
FEATURE                  Location/Qualifiers
source                   1..22
                         mol_type = unassigned RNA
                         organism = Homo sapiens
SEQUENCE: 67
cacacactgc aattactttt gc                                       22

SEQ ID NO: 68            moltype = RNA  length = 21
FEATURE                  Location/Qualifiers
source                   1..21
                         mol_type = unassigned RNA
                         organism = Homo sapiens
SEQUENCE: 68
aaactactga aaatcaaaga t                                        21

SEQ ID NO: 69            moltype = RNA  length = 95
FEATURE                  Location/Qualifiers
source                   1..95
                         mol_type = unassigned RNA
                         organism = Homo sapiens
SEQUENCE: 69
gacaccacat gctcctccag gcctgcctgc cctccaggtc atgttccagt gtcccacaga  60
tgcagcacca cggcccaggc ggcattggtg tcacc                             95
```

-continued

```
SEQ ID NO: 70          moltype = RNA  length = 97
FEATURE                Location/Qualifiers
source                 1..97
                       mol_type = unassigned RNA
                       organism = Homo sapiens
SEQUENCE: 70
ccaccacggt gctggcacca gggcctctgc cccgtaggac accgaggctt atgaatagga  60
gcagtgccgg ccaaggcgcc ggcaccatct tggtgat                           97

SEQ ID NO: 71          moltype = RNA  length = 22
FEATURE                Location/Qualifiers
source                 1..22
                       mol_type = unassigned RNA
                       organism = Homo sapiens
SEQUENCE: 71
tgggaaagag aaagaacaag ta                                           22

SEQ ID NO: 72          moltype = RNA  length = 22
FEATURE                Location/Qualifiers
source                 1..22
                       mol_type = unassigned RNA
                       organism = Homo sapiens
SEQUENCE: 72
tcgggcctgg ggttggggga gc                                           22

SEQ ID NO: 73          moltype = RNA  length = 59
FEATURE                Location/Qualifiers
source                 1..59
                       mol_type = unassigned RNA
                       organism = Homo sapiens
SEQUENCE: 73
cgggctctgg gtgcagtggg ggttcccacg ccgcggcaac caccactgtc tctccccag   59

SEQ ID NO: 74          moltype = RNA  length = 25
FEATURE                Location/Qualifiers
source                 1..25
                       mol_type = unassigned RNA
                       organism = Homo sapiens
SEQUENCE: 74
taggggtggg ggaattcagg ggtgt                                        25

SEQ ID NO: 75          moltype = RNA  length = 20
FEATURE                Location/Qualifiers
source                 1..20
                       mol_type = unassigned RNA
                       organism = Homo sapiens
SEQUENCE: 75
tccccaaccc ctgcccgcag                                              20

SEQ ID NO: 76          moltype = RNA  length = 61
FEATURE                Location/Qualifiers
source                 1..61
                       mol_type = unassigned RNA
                       organism = Homo sapiens
SEQUENCE: 76
gtgcggaacg ctggccgggg cgggagggga agggacgccc ggccggaacg ccgcactcac  60
g                                                                  61

SEQ ID NO: 77          moltype = RNA  length = 21
FEATURE                Location/Qualifiers
source                 1..21
                       mol_type = unassigned RNA
                       organism = Homo sapiens
SEQUENCE: 77
acaccctctt tccctaccgc c                                            21

SEQ ID NO: 78          moltype = RNA  length = 22
FEATURE                Location/Qualifiers
source                 1..22
                       mol_type = unassigned RNA
                       organism = Homo sapiens
SEQUENCE: 78
cagagggaat acagagggca at                                           22

SEQ ID NO: 79          moltype = RNA  length = 67
FEATURE                Location/Qualifiers
source                 1..67
                       mol_type = unassigned RNA
                       organism = Homo sapiens
```

```
SEQUENCE: 79
tggagctgtg tgcagggcca gcgcggagcc cgagcagccg cggtgaagcg cctgtgctct  60
gccgaga                                                            67

SEQ ID NO: 80          moltype = RNA  length = 20
FEATURE                Location/Qualifiers
source                 1..20
                       mol_type = unassigned RNA
                       organism = Homo sapiens
SEQUENCE: 80
tgtgacccta gaataattac                                              20

SEQ ID NO: 81          moltype = RNA  length = 22
FEATURE                Location/Qualifiers
source                 1..22
                       mol_type = unassigned RNA
                       organism = Homo sapiens
SEQUENCE: 81
cgggactgta gagggcatga gc                                           22

SEQ ID NO: 82          moltype = RNA  length = 80
FEATURE                Location/Qualifiers
source                 1..80
                       mol_type = unassigned RNA
                       organism = Homo sapiens
SEQUENCE: 82
ccttgctgat ggcagatgtc ggatctgcct cgcttatacg tgcccttgct gatggcagat  60
gtcgggtctg cctcgcttat                                              80

SEQ ID NO: 83          moltype = RNA  length = 82
FEATURE                Location/Qualifiers
source                 1..82
                       mol_type = unassigned RNA
                       organism = Homo sapiens
SEQUENCE: 83
aaggagcact cactccaatt tccctggact gggggcaggc tgccacctcc tggggacagg  60
ggattggggc aggatgttcc ag                                           82

SEQ ID NO: 84          moltype = RNA  length = 77
FEATURE                Location/Qualifiers
source                 1..77
                       mol_type = unassigned RNA
                       organism = Homo sapiens
SEQUENCE: 84
tgcaatgccc tactcagaaa ggtgccattt atgtagattt tatgtcactg gctcctttct  60
gggtagagca aggctca                                                 77

SEQ ID NO: 85          moltype = RNA  length = 22
FEATURE                Location/Qualifiers
source                 1..22
                       mol_type = unassigned RNA
                       organism = Homo sapiens
SEQUENCE: 85
acagtagagg gaggaatcgc ag                                           22

SEQ ID NO: 86          moltype = RNA  length = 20
FEATURE                Location/Qualifiers
source                 1..20
                       mol_type = unassigned RNA
                       organism = Homo sapiens
SEQUENCE: 86
gtgagtcagg gtggggctgg                                              20

SEQ ID NO: 87          moltype = RNA  length = 69
FEATURE                Location/Qualifiers
source                 1..69
                       mol_type = unassigned RNA
                       organism = Homo sapiens
SEQUENCE: 87
agaggcttgg gccgccgagc tggacccgga ccggttttgg gtactgtact gggggcaggg  60
cagagaggg                                                          69

SEQ ID NO: 88          moltype = RNA  length = 106
FEATURE                Location/Qualifiers
source                 1..106
                       mol_type = unassigned RNA
                       organism = Homo sapiens
```

-continued

```
SEQUENCE: 88
gtgctcgctt cggcagcaca tatactaaaa ttggaacgat acagagaaga ttagcatggc  60
ccctgcgcaa ggatgacacg caaattcgtg aagcgttcca tatttt                106
```

CIRCULATING SERUM MICRORNA BIOMARKERS AND METHODS

This application is a divisional of U.S. patent application Ser. No. 16/075,354 filed Aug. 3, 2018 which claims benefit of PCT Application No. PCT/US2017/016412 filed Feb. 3, 2017, which in turn claims benefit of U.S. Provisional Application No. 62/291,619 filed Feb. 5, 2016. The instant application contains a Sequence Listing which has been submitted electronically in XML format and is hereby incorporated by reference in its entirety. Said XML copy, created on May 15, 2023, is named 140415_567636_SL.xml and is 80,321 bytes in size.

BACKGROUND OF THE INVENTION

1. Field of the Invention

The present invention generally relates to serum-based microRNAs and methods for differentiating patients suffering from Parkinson's disease, as well as assisting clinicians to determine treatment protocols for such patients.

2. Brief Description of the Background Art

Parkinson's Disease (PD) is a highly specific degeneration of dopamine-containing cells of the substantia nigra of the midbrain, causing a dopamine deficiency in the striatum. PD currently affects about 10 million people world-wide. Effective management of a patient with PD is possible in the first 5-7 years of treatment, after which time a series of often debilitating complications, together referred to as Late Motor Fluctuations (LMF) occur. It is believed that treatment with levodopa ((−)-L-α-amino-beta-(3,4-dihydroxy-benzene) propanoic acid), or L-dopa, the most effective antiparkinson drug, may facilitate or even promote the appearance of LMF. Dopamine agonists are employed as a treatment alternative, but they do not offer the same degree of symptomatic relief to patients as L-dopa does.

Symptomatic therapies improve signs and symptoms without affecting the underlying disease state. Levodopa increases dopamine concentration in the striatum, especially when its peripheral metabolism is inhibited by a peripheral decarboxylase inhibitor (PDI). Levodopa/PDI therapy is widely used for symptomatic therapy for Parkinson's disease, such as combinations with levodopa, with carbidopa ((−)-L-α-hydrazino-α-methyl-beta-(3,4-dihydroxybenzene) propanoic acid monohydrate), levodopa and controlled release carbidopa, levodopa and benserazide, levodopa plus controlled release benserazide (2-Amino-3-hydroxy-propionic acid N'-(2,3,4-trihydroxy-benzyl)-hydrazide).

Catechol-O-methyltransferase (COMT) inhibitors enhance levodopa treatment as they inhibit levodopa's metabolism, enhancing its bioavailability and thereby making more of the drug available in the synaptic cleft for a longer period of time. Examples of COMT inhibitors include tolcapone (3,4-dihydroxy-4'-methyl-5-nitrobenzophenone) and entacapone ((E)-2-cyano-3-(3,4-dihydroxy-5-nitrophenyl)-N,N-diethyl-2-propenamide).

Dopamine agonists provide symptomatic benefit by directly stimulating post-synaptic striatal dopamine receptors. Examples include bromocriptine ((5a)-2-Bromo-12'-hydroxy-2'-(1-methylethyl)-5'-(2-methylpropyl) erg-otaman-3',6',18-trione), pergolide (8β-[(Methylthio)methyl]-6-propylergoline), ropinirole (4-[2-(Dipropylamino)ethyl]-1,3-dihydro-2H-indol-2-one), pramipexole ((S)-4,5,6,7-Tetrahydro-$N^6$-propyl-2,6-benzothiazolediamine), lisuride (N'-[(8α)-9,10-didehydro-6-methylergolin-8-yl]-N,N-diethyl-urea), cabergoline ((8β)-N-[3-(Dimethylamino) propyl]-N-[(ethylamino) carbonyl]-6-(2-propenyl) ergoline-8-carboxamide), apomorphine ((6aR)-5,6,6a,7-Tetrahydro-6-methyl-4H-dibenzo[de,g]quinoline-10,11-diol), sumanirole (5-(methylamino)-5,6-dihydro-4H-imidazo {4,5,1-ij}quinolin-2 (1H)-one), rotigotine ((−)(S)-5,6,7,8-tetrahydro-6-[propyl [2-(2-thienyl)ethyl]amino]-1-naphthol-), talipexole (5,6,7,8-Tetrahydro-6-(2-propenyl)-4H-thiazolo [4,5-d]azepin-2-amine), and dihydroergocriptine (ergotaman-3',6',18-trione,9,10-dihydro-12'-hydroxy-2'-methyl-5'-(phenylmethyl) (5' cc)). Dopamine agonists are effective as monotherapy early in the course of Parkinson's disease and as an adjunct to levodopa in more advanced stages. Unlike levodopa, dopamine agonists directly stimulate post-synaptic dopamine receptors. They do not undergo oxidative metabolism and are not thought to accelerate the disease process.

Amantidine (1-Aminotricyclo(3,3,1,$1^{3,7}$) decane) is an antiviral agent that was discovered by chance to have anti-Parkinsonian activity. Its mechanism of action in PD has not been established, but is believed to work by increasing dopamine release. Patients who receive amantidine either as monotherapy or in combination with levodopa show improvement in akinesia, rigidity and tremor.

Other medications used in the treatment of Parkinson's disease include MAO-B inhibitors. Inhibition of L-dopa metabolism through inactivation of the monoamino oxidase type B (MAO-B) is an effective means of enhancing the efficacy of both endogenous residual dopamine and that exogenously derived from its precursor, L-dopa. Selegiline (methyl-(1-methyl-2-phenyl-ethyl)-prop-2-ynyl-amine) is a MAO-B inhibitor. There is evidence that treatment with selegiline may slow down disease progression in PD by blocking formation of free radicals derived from the oxidative metabolism of dopamine. Other examples of MAO B inhibitors include lazabemide (N-(2-Aminoethyl)-5-chloro-2-pyridinecarboxamide), rasagiline (N-propargyl-1-(R)aminoindan and caroxazone (2-oxo-2H-1,3-benzoxazine-3 (4H)-acetamide).

It is imperative to diagnose individuals with PD at an early stage to increase the efficacy of therapeutic agents. However, there are neither any objective tests nor established biomarkers for diagnosing PD. Moreover, the heterogeneity, subtypes and progression of the disease make it difficult to develop specific therapeutic candidates.

MicroRNAs ("miRNAs) are a class of non-coding RNAs that play key roles in the regulation of gene expression. miRNAs act at the post-transcriptional level and fine-tune the expression of as much as 30% of all mammalian protein-encoding genes. Mature miRNAs are short, single-stranded RNA molecules approximately 22 nucleotides in length. miRNAs may be encoded by multiple loci, and may be organized in tandemly co-transcribed clusters. miRNA genes are transcribed by RNA polymerase II as large primary transcripts (pri-microRNA) that are processed by a protein complex containing the RNase III enzyme Drosha, DGCR8 and other cofactors, to form an approximately 70 nucleotide precursor microRNA (pre-miRNA). (Cathew R W, Cell, 2009; Kim V N, Nat Rev Mol Cel Biol, 2009; Siomi H, Mol Cel, 2010; Bartel D P, Cell, 2004; Lee Y, Nature 2003; Han J, Genes Dev, 2004.) Pre-miRNA is transported to the cytoplasm by Exportin-5 where it is processed by DICER, a second RNase III enzyme, together with TRBP, PACT and Ago2 in the RNA Induced Silencing Complex resulting in miRNA duplexes (Kim V N, Nat Rev Mol Cel Biol, 2009; Gregory R I, Nature 2004; MAcRae I J, PNAS, 2008). The guide strands of miRNA duplexes separate and associate with Ago 2 for incorporation into a ribonuclear particle to form the RNA-induced silencing complex RISC that mediates gene silencing. The mechanisms of miRNA range from direct degradation or silencing of mRNA and repression of translation to post-transcriptional upregulations. (MacRae I J, PNAS, 2008.)

The presence of miRNAs has been reported in body fluids including blood, cerebrospinal fluid (CSF), plasma, serum and saliva at detectable levels. The tissue-specificity of miRNAs suggests their vital and integral role in various physiological processes. The tissue-enrichment promises a new but less explored role as diagnostic biomarker and potential therapeutic target. Circulating miRNAs are understood to originate from passive leakage from damaged tissue as a result of cell lysis or apoptosis, active transport from cells via microvesicles, such as exosomes, or bound within RISC protein complexes (Etheridge et al, 2011). Exosome and osmotic pump-mediated delivery of small RNA molecules to the brain and CNS, respectively, provides a solution to overcoming the limitations of miRNA-based therapies (Alvarez-Erviti et al., 2011; Koval et al, 2013, Hum. Mol. Gen). miRNA has been demonstrated to be exceptionally stable and thus present as powerful candidates to be potential biomarkers (Chen et al, 2008; Grasso, 2014).

SUMMARY OF THE INVENTION

It is an object of the present invention to identify miRNAs relevant to patients suffering from Parkinson's disease.

It is another object of the present invention to provide methods for determining patients suffering from Parkinson's disease.

These objects and others are achieved by the present invention, which provides miRNA biomarkers that may be used singly, in pairs or in combination to determine patients suffering from Parkinson's disease.

DETAILED DESCRIPTION OF THE INVENTION

Methods

Serum Samples Handling and Classification

Figure 1:
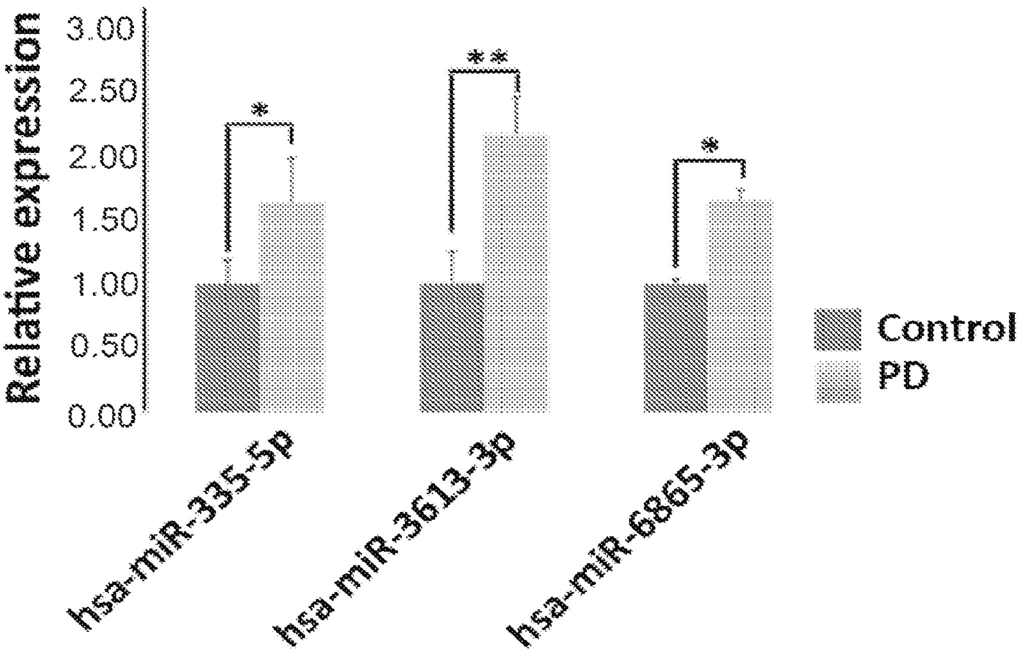
FIG. 1 shows the mean fold change of three PARKmiRNAs between PD patients and healthy controls.

All patients and controls participated in the Norwegian Park West project or the Swedish NYPUM study, which are ongoing prospective population-based longitudinal cohort studies investigating the incidence, neurobiology and prognosis of PD. The Norwegian Park West study is a prospective longitudinal multicenter cohort study of patients with incident Parkinson's disease (PD) from Western and Southern Norway. Between November 1st 2004 and 31st of August 2006 it was endeavored to recruit all new cases of Parkinson Disease within the study area. Since the start of the study 212 of 265 (80%) of these patients and their age-/sex-matched control group have been followed. Further information about this project can be found at the Norwegian Center for Movement Disorders located in Stavanger, Norway. The NYPUM study began in 2004 and endeavours to identify all new cases with idiopathic parkinsonism within the Umeå catchment area and follow them in their disease progression for at least five years. Further information about this study can be found at the Umeå Center for Functional Brain Imaging located in Umeå, Sweden.

All possible efforts were undertaken to establish an unselected and population-representative cohort of patients with PD. Patients were included if they had provided serum at study entry and fulfilled diagnostic criteria for PD of the National Institute of Neurological Disorders and Stroke located in Bethesda Maryland and UK Brain Bank obtainable from the NIH National Library of Medicine in Bethesda, MD at latest follow-up. Patients with secondary parkinsonism at study entry were excluded from this study. Control subjects were recruited from multiple sources, including friends, spouses, and public organizations for elderly and were included in this study if they had provided serum. All patients and controls were Caucasian.

In this study of possible biomarkers for PD we applied a two-stage procedure. For the first discovery phase serum from 16 patients and 8 controls were selected at random. The remaining 164 patients with PD and 182 controls that were eligible for this study were selected for verification purposes.

Serum samples were collected at the same day as the clinical examinations and then stored frozen at −70 degrees Celsius until transported to the facilities in New York on dry ice.

Example 1: Analyses of Differentially Expressed Human miRNA by qPCR

RNA Isolation from Serum Samples and QC

After thawing on ice, twenty-four (eight control, sixteen PD samples) serum samples were spun down for 5 mins at 3000×g to remove debris. The supernatant was used to perform small RNA isolation using miRCURY RNA Isolation Kit—Biofluids (Exiqon, MA). Before RNA Isolation, the lysis buffer was spiked with 0.267 fmol/ul of spike-in control cel-miR-39-3p (Qiagen, CA). The remaining part of the RNA isolation was performed following manufacturer's protocol and the isolated RNA was quantified on a Nanodrop 2000 (Thermo Scientific, MA). The RNA was used for running Affymetrix v4 microRNA microarray chips and for subsequent cDNA synthesis and qPCR. RNA from 434 serum samples (22 control and 42 PD from NYPUM study in addition to 190 control and 180 PD from ParkWest project) was isolated as described above, they were not quantified by Nanodrop, but the qPCR data resulting from these samples were normalized by a reference small RNA scaRNA17.

miRNA Microarray and Data Analysis

The isolated RNA from twenty-four patient serum samples were quantified and subjected to Affymetrix GeneChip® miRNA 4.0 Array by the Yale Center for Genome Analysis. The normalized. CEL files obtained from Affymetrix Expression Console software were imported into Partek Genomics Suite version 6.6 Copyright @ 2012 (Partek, MO) for analysis. The 'microRNA Expression Workflow' was employed to detect differentially expressed miRNAs employing ANOVA resulting in lists of miRNAs significantly ($p<0.05$) expressed between control versus PD cohorts. The miRNAs detected were used for further qPCR verification.

Quantitative Polymerase Chain Reaction cDNA for miRNA specific qPCR was synthesized using qScript™ microRNA cDNA Synthesis kit (Quanta Biosciences, MD) following manufacturer's protocol and subsequent qPCRs were performed using miRNA specific forward primers and PerfeCTa®Universal PCR primer (Quanta Biosciences, MD). scaRNA17 and U6 were used reference small RNAs for normalizing qPCR Cq values whereas cel-miR-39-3p was used as spike-in control. PerfeCTa® SYBR® GREEN SuperMix for IQ™ (Quanta Biosciences, MD) was used for all qPCRs in a MyiQ™ Single color Real-Time PCR Detection System (Bio-Rad, CA). Standard curve for cel-miR-39-3p was analyzed in MS Excel with $R^2=0.97882$ and PCR efficiency 92.96%. No Template Control (NTC) was implied wherever needed.

Data Analysis Based on PD Model

The discriminative ability of miRNAs with regard to PD diagnosis was assessed from ROC analysis using IBM SPSS Statistics, version 21; for combinations of miRNAs the test variable was the predicted probability from logistic regression with PD diagnosis (yes/no) as outcome. To minimize the influence of outlying values on the fit, logistic regression was performed with log transformed miRNA values.

Differentially expressed human miRNAs in Parkinson's disease patients' serum samples from The Norwegian ParkWest study were determined employing miRNA microarray. Provided below are the miRNAs with >1.2 fold differential expression.

85 Differentially Expressed Human Pre- and Mature miRNAs with >1.2 Fold Change hsa-miR-548ac, hsa-miR-335-5p, hsa-miR-548x-3p, hsa-miR-520g, hsa-miR-520h, hsa-miR-548ae, hsa-miR-3910-1, hsa-miR-4708-3p, hsa-miR-16-2-3p, hsa-miR-603, hsa-miR-3613-3p, hsa-miR-4797-5p, hsa-miR-548aj-3p, hsa-miR-450b-5p, hsa-miR-548ap-3p, hsa-miR-1184, hsa-miR-2277-5p, hsa-miR-1323, hsa-miR-548aa, hsa-miR-548t-3p, hsa-miR-221-5p, hsa-miR-190a-3p, hsa-miR-6873-5p, hsa-miR-155-3p, hsa-miR-510-5p, hsa-miR-4313, hsa-miR-3616, hsa-miR-8075, hsa-miR-4306, hsa-miR-6776, hsa-miR-6075, hsa-miR-8052, hsa-miR-532, hsa-miR-4791, hsa-miR-320b-1, hsa-miR-548y, hsa-miR-7973, hsa-miR-3136-5p, hsa-miR-606, hsa-miR-500a-3p, hsa-miR-4788, hsa-miR-4769-3p, hsa-miR-299-5p, hsa-miR-4431, hsa-miR-6749-5p, hsa-miR-138-2-3p, hsa-miR-1289-2, hsa-miR-548au, hsa-miR-6850, hsa-miR-561, hsa-miR-34b-5p, hsa-miR-3934-5p, hsa-miR-6739-5p, hsa-miR-4325, hsa-miR-4672, hsa-miR-215-5p, hsa-miR-4685-5p, hsa-miR-3160-1, hsa-miR-3160-2, hsa-miR-6793-5p, hsa-miR-8089, hsa-miR-6081, hsa-miR-892b, hsa-miR-936, hsa-miR-548ag, hsa-miR-345, hsa-miR-548k, hsa-miR-3188, hsa-miR-181b-5p, hsa-let-7e, hsa-miR-4487, hsa-miR-509-3p, hsa-miR-3689a-3p, hsa-miR-4771, hsa-miR-520a-5p, hsa-miR-3150b, hsa-miR-6782-5p, hsa-miR-937-5p, hsa-miR-455-3p, hsa-miR-6865-3p, hsa-miR-4749-5p, hsa-miR-378b, hsa-miR-7706, hsa-miR-4445 and hsa-miR-2355-5p.

57 differentially expressed mature miRNAs with >1.2 fold change hsa-miR-548ac, hsa-miR-335-5p, hsa-miR-548x-3p, hsa-miR-548ae, hsa-miR-4708-3p, hsa-miR-16-2-3p, hsa-miR-603, hsa-miR-3613-3p, hsa-miR-4797-5p, hsa-miR-548aj-3p, hsa-miR-450b-5p, hsa-miR-548ap-3p, hsa-miR-1184, hsa-miR-2277-5p, hsa-miR-1323, hsa-miR-548aa, hsa-miR-548t-3p, hsa-miR-221-5p, hsa-miR-190a-3p, hsa-miR-6873-5p, hsa-miR-155-3p, hsa-miR-510-5p, hsa-miR-4313, hsa-miR-4306, hsa-miR-8052, hsa-miR-4791, hsa-miR-7973, hsa-miR-3136-5p, hsa-miR-606, hsa-miR-500a-3p, hsa-miR-4769-3p, hsa-miR-299-5p, hsa-miR-6749-5p, hsa-miR-138-2-3p, hsa-miR-34b-5p, hsa-miR-3934-5p, hsa-miR-6739-5p, hsa-miR-4325, hsa-miR-215-5p, hsa-miR-4685-5p, hsa-miR-6793-5p, hsa-miR-936, hsa-miR-548ag, hsa-miR-548k, hsa-miR-181b-5p, hsa-let-7e, hsa-miR-509-3p, hsa-miR-3689a-3p, hsa-miR-4771, hsa-miR-520a-5p, hsa-miR-6782-5p, hsa-miR-937-5p, hsa-miR-455-3p, hsa-miR-6865-3p, hsa-miR-4749-5p, hsa-miR-378b and hsa-miR-2355-5p.

28 differentially expressed premature miRNAs with >1.2 fold change hsa-miR-520g, hsa-miR-520h, hsa-miR-3910-1, hsa-miR-3616, hsa-miR-8075, hsa-miR-6776, hsa-miR-6075, hsa-miR-532, hsa-miR-320b-1, hsa-miR-548y, hsa-miR-4788, hsa-miR-4431, hsa-miR-1289-2, hsa-miR-548au, hsa-miR-6850, hsa-miR-561, hsa-miR-4672, hsa-miR-3160-1, hsa-miR-3160-2, hsa-miR-8089, hsa-miR-6081, hsa-miR-892b, hsa-miR-345, hsa-miR-3188, hsa-miR-4487, hsa-miR-3150b, hsa-miR-7706 and hsa-miR-4445.

These differentially expressed miRNA sequences are illustrated below in Table 1, along with the reference/housekeeping small RNAs cel-miR-39-3p, U6 and ScaRNA17 used as controls. Cel-miR-39-3p is a spike-in control that demonstrates the stability of the RNA samples. U6 and ScaRNA17 are used as internal controls to normalize the readings of the rest of the miRNAs or candidate miRNAs.

TABLE 1

| RNA name | microRNA Sequence |
| --- | --- |
| cel-miR-39-3p | UCACCGGGUGUAAAUCAGCUUG (SEQ ID NO: 1) |
| hsa-let-7e | UGAGGUAGGAGGUUGUAUAGUU (SEQ ID NO: 2) |
| hsa-miR-1184 | CCUGCAGCGACUUGAUGGCUUCC (SEQ ID NO: 3) |
| hsa-miR-1289-2 | CCACGGUCCUAGUUAAAAAGGCACAUUCCUAGACCCUGCCUC AGAACUACUGAACAGAGUCACUGGGUGUGGAGUCCAGGAAUC UGCAUUUUUACCCCUAUCGCCCCCGCC (SEQ ID NO: 4) |

TABLE 1-continued

| RNA name | microRNA Sequence |
|---|---|
| hsa-miR-1323 | UCAAAACUGAGGGGCAUUUUCU (SEQ ID NO: 5) |
| hsa-miR-138-2-3p | GCUAUUUCACGACACCAGGGUU (SEQ ID NO: 6) |
| hsa-miR-155-3p | CUCCUACAUAUUAGCAUUAACA (SEQ ID NO: 7) |
| hsa-miR-16-2-3p | CCAAUAUUACUGUGCUGCUUUA (SEQ ID NO: 8) |
| hsa-miR-181b-5p | AACAUUCAUUGCUGUCGGUGGGU (SEQ ID NO: 9) |
| hsa-miR-190a-3p | CUAUAUAUCAAACAUAUUCCU (SEQ ID NO: 10) |
| hsa-miR-215-5p | AUGACCUAUGAAUUGACAGAC (SEQ ID NO: 11) |
| hsa-miR-221-5p | ACCUGGCAUACAAUGUAGAUUU (SEQ ID NO: 12) |
| hsa-miR-2277-5p | AGCGCGGGCUGAGCGCUGCCAGUC (SEQ ID NO: 13) |
| hsa-miR-2355-5p | AUCCCCAGAUACAAUGGACAA (SEQ ID NO: 14) |
| hsa-miR-299-5p | UGGUUUACCGUCCCACAUACAU (SEQ ID NO: 15) |
| hsa-miR-3136-5p | CUGACUGAAUAGGUAGGGUCAUU (SEQ ID NO: 16) |
| hsa-miR-3150b | GAGGGAAAGCAGGCCAACCUCGAGGAUCUCCCCAGCCUUGGC GUUCAGGUGCUGAGGAGAUCGUCGAGGUUGGCCUGCUUCCCC UC (SEQ ID NO: 17) |
| hsa-miR-3160-1 | GGACCUGCCCUGGGCUUUCUAGUCUCAGCUCUCCUCCAGCUC AGCUGGUCAGGAGAGCUGAGACUAGAAAGCCCAGGGCAGGUU C (SEQ ID NO: 18) |
| hsa-miR-3160-2 | ACCUGCCCUGGGCUUUCUAGUCUCAGCUCUCCUGACCAGCUG AGCUGGAGGAGAGCUGAGACUAGAAAGCCCAGGGCAGGU (SEQ ID NO: 19) |
| hsa-miR-3188 | GGCGCCUCCUGCUCUGCUGUGCCGCCAGGGCCUCCCCUAGCGC GCCUUCUGGAGAGGCUUUGUGCGGAUACGGGGCUGGAGGCCU (SEQ ID NO: 20) |
| hsa-miR-320b-1 | AAUUAAUCCCUCUCUUUCUAGUUCUUCCUAGAGUGAGGAAAA GCUGGGUUGAGAGGGCAAACAAAUUAACUAAUUAAUU (SEQ ID NO: 21) |
| hsa-miR-335-5p | UCAAGAGCAAUAACGAAAAAUGU (SEQ ID NO: 22) |
| hsa-miR-345 | ACCCAAACCCUAGGUCUGCUGACUCCUAGUCCAGGGCUCGUG AUGGCUGGUGGGCCCUGAACGAGGGGUCUGGAGGCCUGGGUU UGAAUAUCGACAGC (SEQ ID NO: 23) |
| hsa-miR-34b-5p | UAGGCAGUGUCAUUAGCUGAUUG (SEQ ID NO: 24) |
| hsa-miR-3613-3p | ACAAAAAAAAAAGCCCAACCCUUC (SEQ ID NO: 25) |
| hsa-miR-3616 | UGUCACUCCGCCAGCAUCAUGAAGUGCACUCAUGAUAUGUUU GCCCCAUCAGCGUGUCACGAGGGCAUUUCAUGAUGCAGGCGG GGUUGGCA (SEQ ID NO: 26) |
| hsa-miR-3689a-3p | CUGGGAGGUGUGAUAUCGUGGU (SEQ ID NO: 27) |
| hsa-miR-378b | ACUGGACUUGGAGGCAGAA (SEQ ID NO: 28) |
| hsa-miR-3910-1 | CUUUUGCUGUCAGUUUUUCUGUUGCUUGUCUUGGUUUUAUGC CUUUUAUAUCAAGGCACAUAAAAGGCAUAAAACCAAGACAAG CAACAAAAAAAGGAUUGAUCACAGAAG (SEQ ID NO: 29) |
| hsa-miR-3934-5p | UCAGGUGUGGAAACUGAGGCAG (SEQ ID NO: 30) |
| hsa-miR-4306 | UGGAGAGAAAGGCAGUA (SEQ ID NO: 31) |
| hsa-miR-4313 | AGCCCCCUGGCCCCAAACCC (SEQ ID NO: 32) |
| hsa-miR-4325 | UUGCACUUGUCUCAGUGA (SEQ ID NO: 33) |
| hsa-miR-4431 | UGGUUUGCGACUCUGAAAACUAGAAGGUUUAUGACUGGGCA UUUCUCACCCAAUGCCCAAUAUUGAACUUUCUAGUUGUCAGA GUCAUUAACCC (SEQ ID NO: 34) |

TABLE 1-continued

| RNA name | microRNA Sequence |
|---|---|
| hsa-miR-4445 | UUCCUGCAGAUUGUUUCUUUUGCCGUGCAAGUUUAAGUUUUU GCACGGCAAAAGAAACAAUCCAGAGGGU (SEQ ID NO: 35) |
| hsa-miR-4487 | ACUGUCCUUCAGCCAGAGCUGGCUGAAGGGCAGAAGGGAACU GUCCUUCAGCCAGAGCUGGCUGAAGGGCAGA (SEQ ID NO: 36) |
| hsa-miR-450b-5p | UUUUGCAAUAUGUUCCUGAAUA (SEQ ID NO: 37) |
| hsa-miR-455-3p | GCAGUCCAUGGGCAUAUACAC (SEQ ID NO: 38) |
| hsa-miR-4672 | GGCUGCUUCUCGCCUCUGUCCAGCUGUGUGGCCUUGGACAAG CCUCUUGGUUACACAGCUGGACAGAGGCACGAAACAGCC (SEQ ID NO: 39) |
| hsa-miR-4685-5p | CCCAGGGCUUGGAGUGGGGCAAGGUU (SEQ ID NO: 40) |
| hsa-miR-4708-3p | AGCAAGGCGGCAUCUCUCUGAU (SEQ ID NO: 41) |
| hsa-miR-4749-5p | UGCGGGGACAGGCCAGGGCAUC (SEQ ID NO: 42) |
| hsa-miR-4769-3p | UCUGCCAUCCUCCCUCCCCUAC (SEQ ID NO: 43) |
| hsa-miR-4771 | AGCAGACUUGACCUACAAUUA (SEQ ID NO: 44) |
| hsa-miR-4788 | AAUGAAGGAUUACGGACCAGCUAAGGGAGGCAUUAGGAUC CUUAUUCUUGCCUCCCUUAGUUGGUCCCUAAUCCUUCGUU (SEQ ID NO: 45) |
| hsa-miR-4791 | UGGAUAUGAUGACUGAAA (SEQ ID NO: 46) |
| hsa-miR-4797-5p | GACAGAGUGCCACUUACUGAA (SEQ ID NO: 47) |
| hsa-miR-500a-3p | AUGCACCUGGGCAAGGAUUCUG (SEQ ID NO: 48) |
| hsa-miR-509-3p | UGAUUGGUACGUCUGUGGGUAG (SEQ ID NO: 49) |
| hsa-miR-510-5p | UACUCAGGAGAGUGGCAAUCAC (SEQ ID NO: 50) |
| hsa-miR-520a-5p | CUCCAGAGGGAAGUACUUUCU (SEQ ID NO: 51) |
| hsa-miR-520g | UCCCAUGCUGUGACCCUCUAGAGGAAGCACUUUCUGUUUGUU GUCUGAGAAAAAACAAAGUGCUUCCCUUUAGAGUGUUACCGU UUGGGA (SEQ ID NO: 52) |
| hsa-miR-520h | UCCCAUGCUGUGACCCUCUAGAGGAAGCACUUUCUGUUUGUU GUCUGAGAAAAAACAAAGUGCUUCCCUUUAGAGUUACUGUUU GGGA (SEQ ID NO: 53) |
| hsa-miR-532 | CGACUUGCUUUCUCUCCUCCAUGCCUUGAGUGUAGGACCGUU GGCAUCUUAAUUACCCUCCCACACCCAAGGCUUGCAGAAGAG CGAGCCU (SEQ ID NO: 54) |
| hsa-miR-548aa | AAAAACCACAAUUACUUUUGCACCA (SEQ ID NO: 55) |
| hsa-miR-548ac | CAAAAACCGGCAAUUACUUUUG (SEQ ID NO: 56) |
| hsa-miR-548ae | CAAAAACUGCAAUUACUUUCA (SEQ ID NO: 57) |
| hsa-miR-548ag | AAAGGUAAUUGUGGUUUCUGC (SEQ ID NO: 58) |
| hsa-miR-548aj-3p | UAAAAACUGCAAUUACUUUUA (SEQ ID NO: 59) |
| hsa-miR-548ap-3p | AAAAACCACAAUUACUUUU (SEQ ID NO: 60) |
| hsa-miR-548au | AAAAGUAAUUGCGGUUUUUGCUAUUGGUUUUAAUGGCAGUU ACUUUUGCACCAG (SEQ ID NO: 61) |
| hsa-miR-548k | AAAAGUACUUGCGGAUUUUGCU (SEQ ID NO: 62) |
| hsa-miR-548t-3p | AAAAACCACAAUUACUUUUGCACCA (SEQ ID NO: 63) |
| hsa-miR-548x-3p | UAAAAACUGCAAUUACUUUC (SEQ ID NO: 64) |
| hsa-miR-548y | GCCUAAACUAUUAGGUUGGUGCAAAAGUAAUCACUGUUUUU GCCAUUACUCUCAGUGGCAAAAACCGUGAUUACUUUUGCACC AACCUAGUAACACCUUCACUGUGGGGG (SEQ ID NO: 65) |

TABLE 1-continued

| RNA name | microRNA Sequence |
|---|---|
| hsa-miR-561 | CUUCAUCCACCAGUCCUCCAGGAACAUCAAGGAUCUUAAACU UUGCCAGAGCUACAAAGGCAAAGUUUAAGAUCCUUGAAGUUC CUGGGGGAACCAU (SEQ ID NO: 66) |
| hsa-miR-603 | CACACACUGCAAUUACUUUUGC (SEQ ID NO: 67) |
| hsa-miR-606 | AAACUACUGAAAAUCAAAGAU (SEQ ID NO: 68) |
| hsa-miR-6075 | GACACCACAUGCUCCUCCAGGCCUGCCUGCCCUCCAGGUCAU GUUCCAGUGUCCCACAGAUGCAGCACCACGGCCCAGGCGGCA UUGGUGUCACC (SEQ ID NO: 69) |
| hsa-miR-6081 | CCACCACGGUGCUGGCACCAGGGCCUCUGCCCCGUAGGACAC CGAGGCUUAUGAAUAGGAGCAGUGCCGGCCAAGGCGCCGGCA CCAUCUUGGUGAU (SEQ ID NO: 70) |
| hsa-miR-6739-5p | UGGGAAAGAGAAAGAACAAGUA (SEQ ID NO: 71) |
| hsa-miR-6749-5p | UCGGGCCUGGGGUUGGGGGAGC (SEQ ID NO: 72) |
| hsa-miR-6776 | CGGGCUCUGGGUGCAGUGGGGGUUCCCACGCCGCGGCAACCA CCACUGUCUCUCCCCAG (SEQ ID NO: 73) |
| hsa-miR-6782-5p | UAGGGGUGGGGGAAUUCAGGGGUGU (SEQ ID NO: 74) |
| hsa-miR-6793-5p | UCCCCAACCCCUGCCCGCAG (SEQ ID NO: 75) |
| hsa-miR-6850 | GUGCGGAACGCUGGCCGGGGCGGGAGGGGAAGGGACGCCCGG CCGGAACGCCGCACUCACG (SEQ ID NO: 76) |
| hsa-miR-6865-3p | ACACCCUCUUUCCCUACCGCC (SEQ ID NO: 77) |
| hsa-miR-6873-5p | CAGAGGGAAUACAGAGGGCAAU (SEQ ID NO: 78) |
| hsa-miR-7706 | UGGAGCUGUGUGCAGGGCCAGCGCGGAGCCCGAGCAGCCGCG GUGAAGCGCCUGUGCUCUGCCGAGA (SEQ ID NO: 79) |
| hsa-miR-7973 | UGUGACCCUAGAAUAAUUAC (SEQ ID NO: 80) |
| hsa-miR-8052 | CGGGACUGUAGAGGGCAUGAGC (SEQ ID NO: 81) |
| hsa-miR-8075 | CCUUGCUGAUGGCAGAUGUCGGAUCUGCCUCGCUUAUACGUG CCCUUGCUGAUGGCAGAUGUCGGGUCUGCCUCGCUUAU (SEQ ID NO: 82) |
| hsa-miR-8089 | AAGGAGCACUCACUCCAAUUUCCCUGGACUGGGGGCAGGCUG CCACCUCCUGGGGACAGGGGAUUGGGGCAGGAUGUUCCAG (SEQ ID NO: 83) |
| hsa-miR-892b | UGCAAUGCCCUACUCAGAAAGGUGCCAUUUAUGUAGAUUUUA UGUCACUGGCUCCUUUCUGGGUAGAGCAAGGCUCA (SEQ ID NO: 84) |
| hsa-miR-936 | ACAGUAGAGGGAGGAAUCGCAG (SEQ ID NO: 85) |
| hsa-miR-937-5p | GUGAGUCAGGGUGGGGCUGG (SEQ ID NO: 86) |
| scaRNA17 | AGAGGCUUGGGCCGCCGAGCUGGACCCGGACCGGUUUUGGGU ACUGUACUGGGGGCAGGGCAGAGAGGG (SEQ ID NO: 87) |
| U6 | GUGCUCGCUUCGGCAGCACAUAUACUAAAAUUGGAACGAUAC AGAGAAGAUUAGCAUGGCCCCUGCGCAAGGAUGACACGCAAA UUCGUGAAGCGUUCCAUAUUUU (SEQ ID NO: 88) |

Example 2: Verification of Human Mature miRNAs by qPCR in Sample Cohort of 16 Patients and 8 Controls The mean fold change for hsa-miR-335-5p, hsa-miR-3613-3p and hsa-miR-6865-3p PARKmiRs between PD patients and healthy controls are shown below in Table 2 and illustrated in FIG. 1.

TABLE 2

| PARKmiR | Fold change | Significance |
|---|---|---|
| hsa-miR-335-5p | 1.64 | 0.02 |
| hsa-miR-3613-3p | 2.16 | 0.004 |
| hsa-miR-6865-3p | 1.65 | 0.03 |

Example 3: Analyses of Hsa-miR-335-5p and Hsa-miR-6865-3p in a Cohort of 346 Individuals (182 Control and 164 PD Serum Samples) from Norwegian ParkWest Study The qPCR technique of Example 2 was used to identify potential diagnostic biomarkers. It was determined that combinations of hsa-miR-335-5p and hsa-miR-6865-3p show high predictability for PD diagnosis. The results of the model with hsa-miR-335-5p and hsa-miR-6865-3p, Outcome=PD (YES/NO), n=164 cases+182 controls are shown below in Table 3.

TABLE 3

Statistical analysis of individual and combination of PARKmiRs from 164 PD patients and 182 controls

| miRNA(s) | Patients (n = 164) median (IQR) | Controls (n = 182) median (IQR) | p[1] |
|---|---|---|---|
| 335 | 1.4 (0.5 to 2.7) | 0.12 (0.06 to 0.22) | <0.001 |
| 6865 | 2.7 (1.1 to 6.9) | 1.0 (0.8 to 1.5) | <0.001 |
| 3613 | 0.41 (0.19 to 0.92) | 0.21 (0.09 to 0.49) | <0.001 |
| 335/6865 | | | |
| 335/3613 | | | |

| miRNA(s) | AUC (95% CI) | p[2] |
|---|---|---|
| 335 | 0.90 (0.87 to 0.93) | <0.001 |
| 6865 | 0.74 (0.69 to 0.80) | <0.001 |
| 3613 | 0.65 (0.59 to 0.71) | <0.001 |
| 335/6865 | 0.90 (0.87 to 0.93) | <0.001 |
| 335/3613 | 0.90 (0.87 to 0.94) | <0.001 |

Figure 2A:
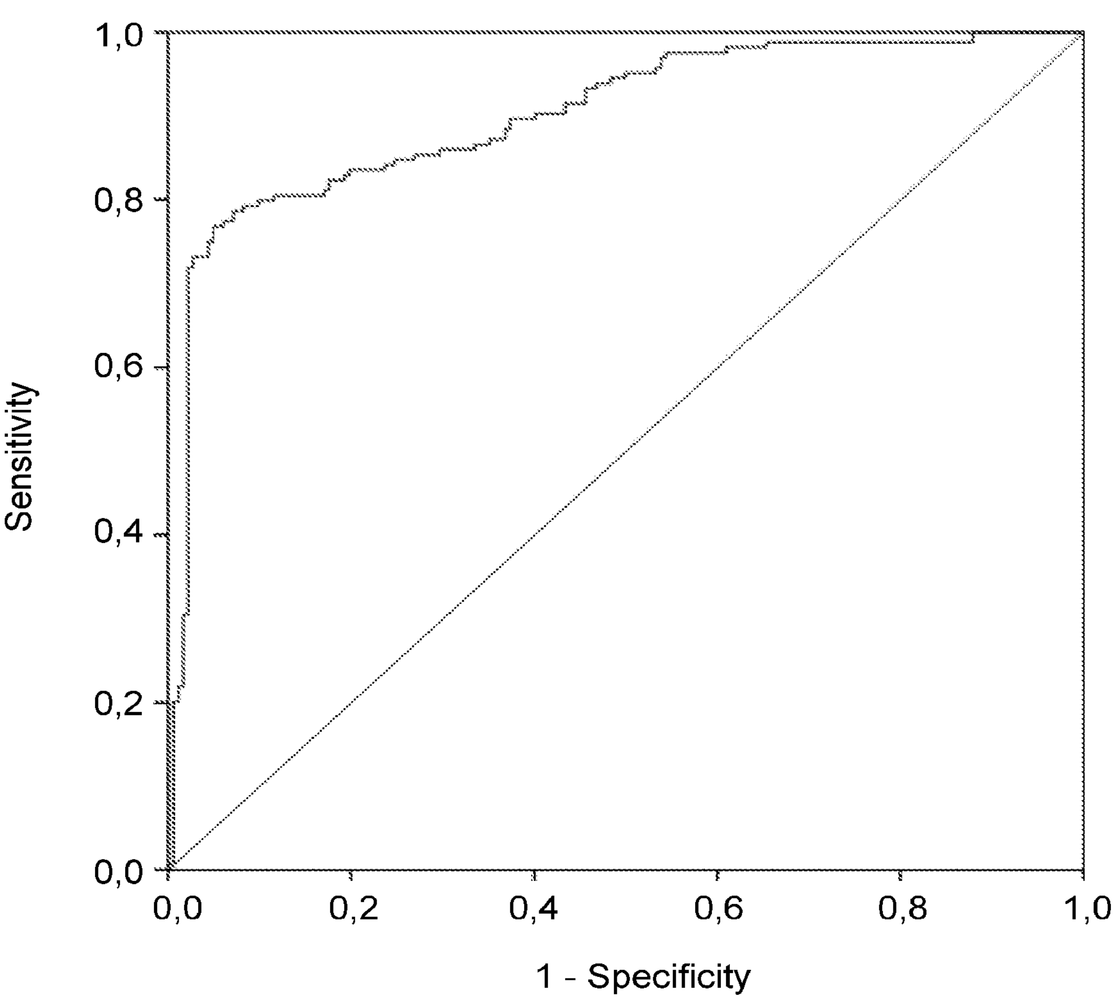
FIG. 2A is a ROC analysis based on predicted probabilities from the model and compared to true disease status.

ROC analysis based on predicted probabilities compared to true disease status is depicted in FIG. 2*a*, and show strong discriminating ability. The area under the curve of FIG. 2*a* is provided in Table 3 above.

Example 4: Analyses of Hsa-miR-335-5p and Hsa-miR-3613-3p in a Cohort of 346 Individuals (182 Control and 164 PD Serum Samples)

Following the protocol of Example 3 it was determined that combinations of hsa-miR-335-5p and hsa-miR-3613-3p also show high predictability for PD diagnosis. The results of the model with hsa-miR-335-5p and hsa-miR-3613-3p, Outcome=PD (YES/NO), n=164 cases+182 controls are shown above in Table 3.

Figure 2B:
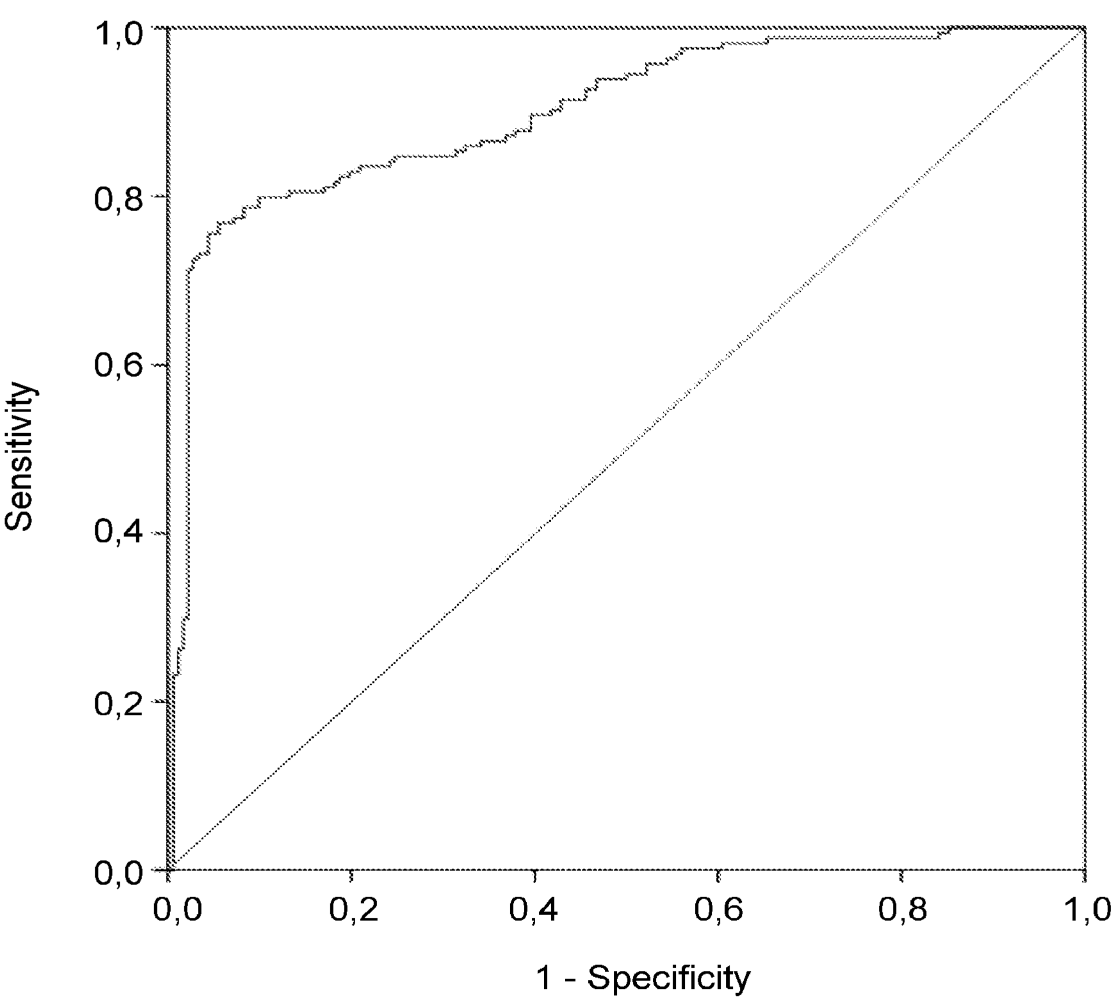
FIG. 2B is a ROC analysis based on predicted prohibition from the model.

ROC analysis based on predicted probabilities from the model showing strong discriminating ability are depicted in FIG. 2*b*. The area under the curve of FIG. 2*b* is provided in Table 3 above.

From the foregoing Examples 1~4 it is evidenced that any combination of two or more microRNAs from the list of 85 identified miRNAs can be used to diagnose the occurrence of PD in patients.

Example 5: hsa-miR-335-5p

Table 3 above illustrates that hsa-miR-335-5p shows high predictability for PD diagnosis for Outcome=PD (YES/NO), n=164 cases+182 controls.

Figure 3:
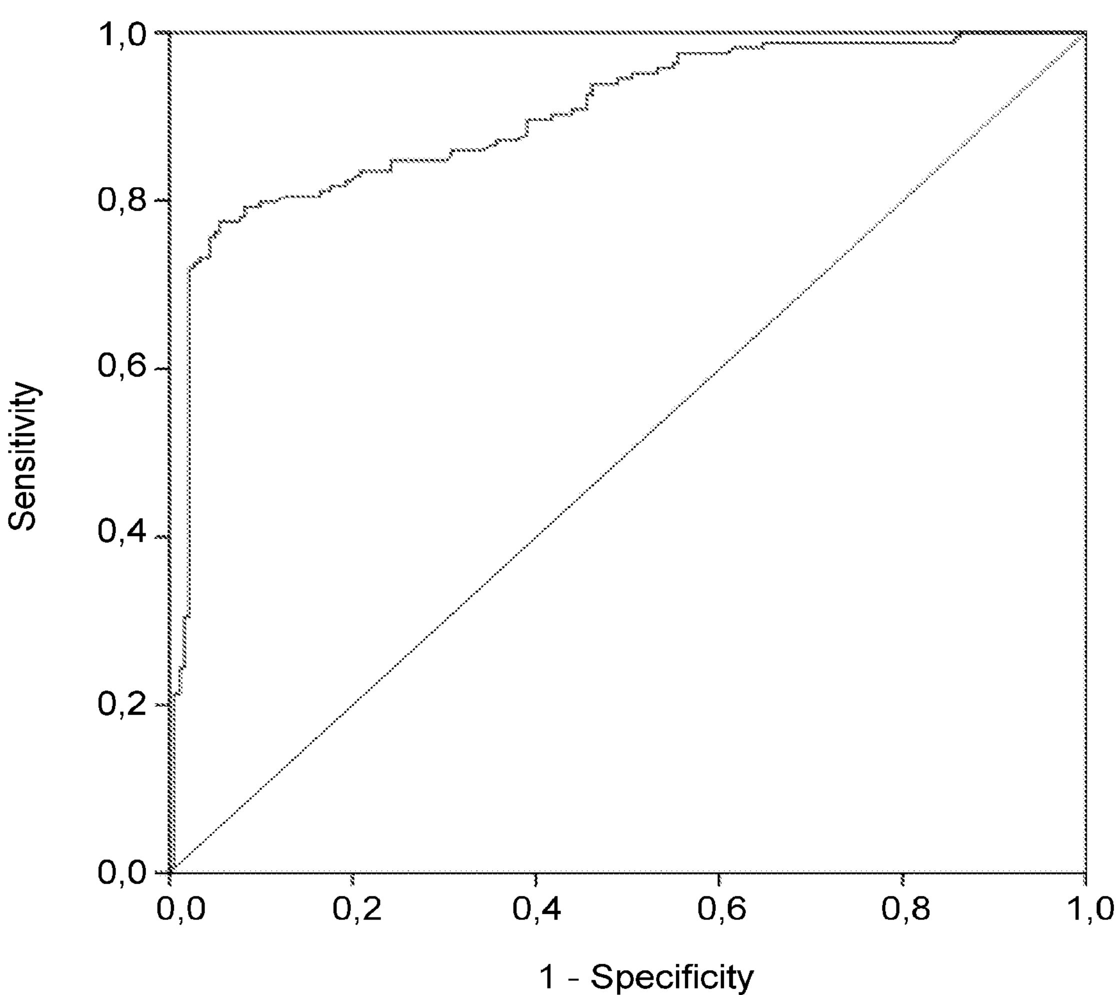
FIG. 3 is a ROC analysis based on predicted probabilities from the model and compared to true disease status.

ROC analysis based on probabilities from the model and compared to true disease status showing strong discriminating ability is shown in FIG. 3. The area under the curve of FIG. 3 is provided in Table 3 above.

Figure 4:
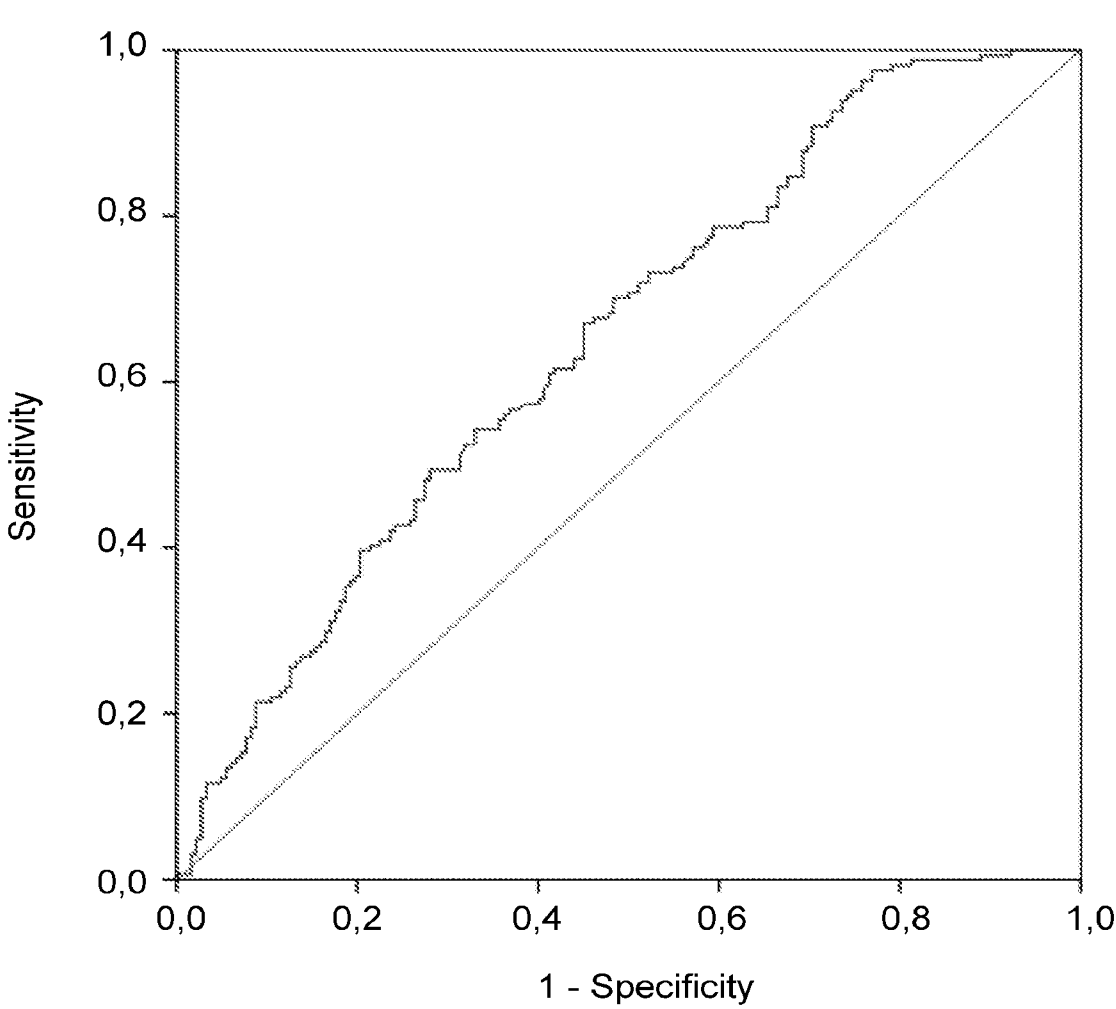
FIG. 4 is a ROC analysis based on predicted probabilities from the model and compared to true disease status.

Example 6: has-miR-3613-3p hsa-miR-3613-3p also shows high predictability for PD diagnosis as illustrated in Table 3 above. ROC analysis based on probabilities from the model and compared to true disease status showing strong discriminating ability is shown in FIG. 4. The area under the curve of FIG. 4 is provided in Table 3 above.

Example 7: has-miR-6865-3p

Figure 5:
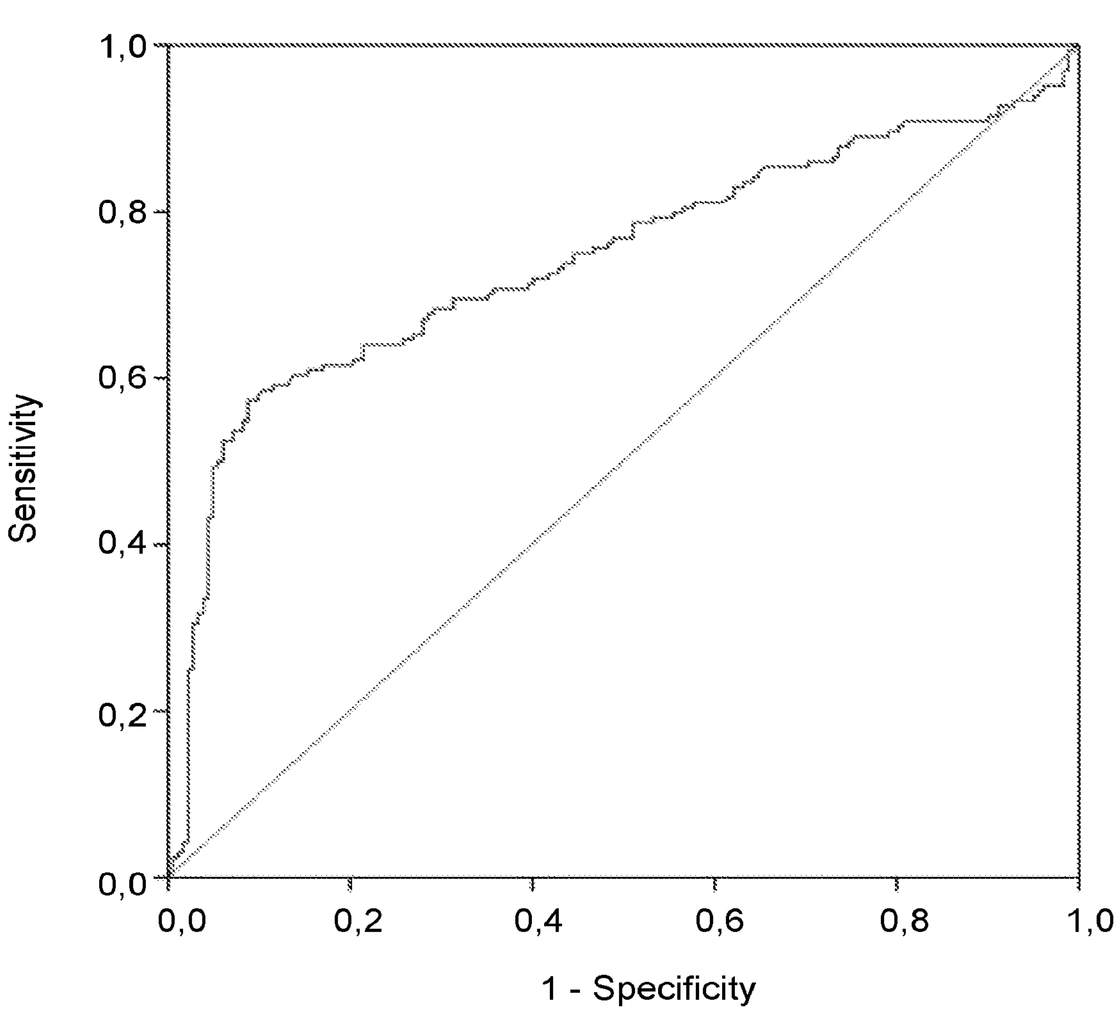
FIG. 5 is a ROC analysis based on predicted probabilities from the model and compared to true disease status.

Similarly, hsa-miR-6865-3p also shows high predictability for PD diagnosis as shown in Table 3 above. ROC analysis based on probabilities from the model and compared to true disease status showing strong discriminating ability is shown in FIG. 5. The area under the curve of FIG. 5 is provided above in Table 3.

From the foregoing Examples 5-7, it is evidenced that hsa-miR-335-5p, hsa-miR-3613-3p and hsa-miR-6865-3p may be used individually for accurate diagnosis of PD.

Example 8: Analyses of Hsa-miR-335-5p and Hsa-miR-6865-3p in a Cohort of 64 Individuals (22 Control and 42 PD Serum Samples) from Swedish NYPUM Study The qPCR technique of Example 2 was used to validate the diagnostic biomarkers of Example 2. It was determined that combinations of hsa-miR-335-5p and hsa-miR-6865-3p show high predictability for PD diagnosis. The results of the model with hsa-miR-335-5p and hsa-miR-6865-3p, Outcome=PD (YES/NO), n=42 cases+22 controls are shown below in Table 4.

TABLE 4

Statistical analysis of individual and combinations of PARKmiRs from 42 PD patients and 22 controls from the NYPUM study.

| miRNA(s) | Patients (n = 42) median (IQR) | Controls (n = 22) median (IQR) | p[1] | AUC (95% CI) | p[2] |
|---|---|---|---|---|---|
| 335 | 1.3 (0.79 to 2.2) | 1.1 (0.71 to 1.4) | 0.125 | 0.62 (0.48 to 0.75) | 0.127 |
| 3613 | 2.1 (1.2 to 3.3) | 1.2 (1.0 to 1.6) | 0.012 | 0.74 (0.62 to 0.86) | 0.002 |
| 6865 | 1.5 (1.2 to 2.2) | 1.2 (1.0 to 1.4) | 0.002 | 0.69 (0.56 to 0.82) | 0.012 |
| 335/3613 | n/a | n/a | n/a | 0.75 (0.63 to 0.87) | 0.001 |
| 335/6865 | n/a | n/a | n/a | 0.71 (0.59 to 0.84) | 0.006 |
| 3613/6865 | n/a | n/a | n/a | 0.75 (0.63 to 0.87) | 0.001 |
| 335/3613/6865 | n/a | n/a | n/a | 0.76 (0.64 to 0.87) | 0.001 |

Figure 7:
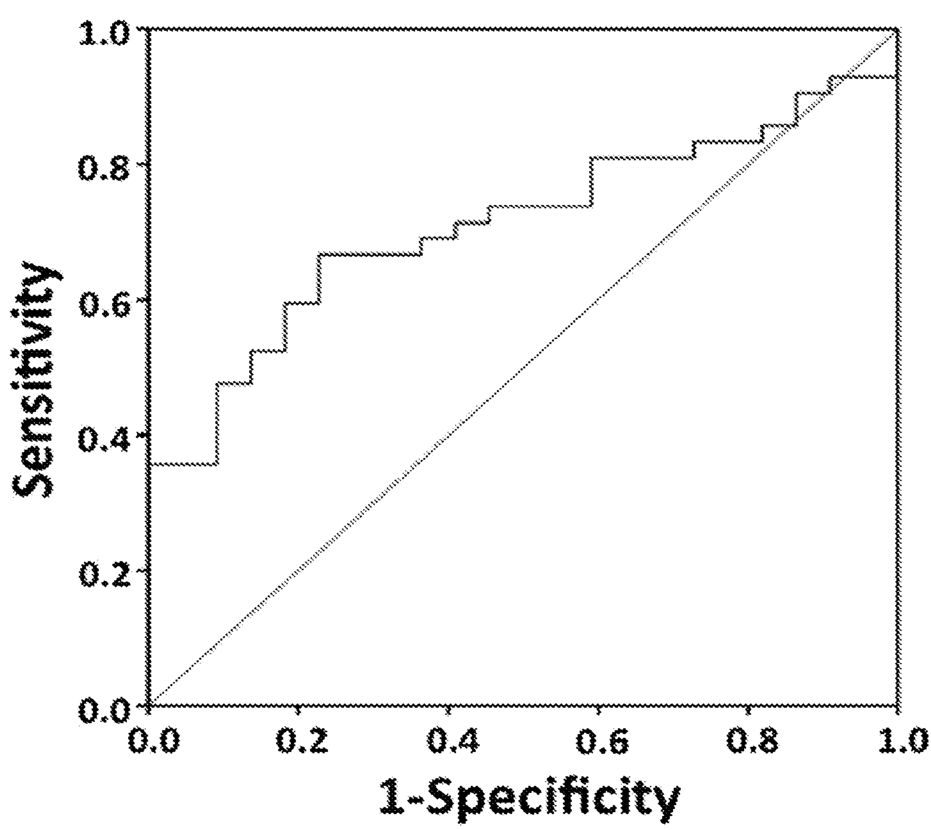
FIG. 7 is a ROC analysis based on predicted probabilities from the model and compared to true disease status.

ROC analysis based on predicted probabilities compared to true disease status is depicted in FIG. 7, and show strong discriminating ability. The area under the curve of FIG. 7 is provided in Table 4 above.

Example 9: Analyses of Hsa-miR-335-5p and Hsa-miR-3613-3p in a Cohort of 64 Individuals (22 Control and 42 PD Serum Samples)

Following the protocol of Example 3 it was determined that combinations of hsa-miR-335-5p and hsa-miR-3613-3p also show high predictability for PD diagnosis. The results of the model with hsa-miR-335-5p and hsa-miR-3613-3p, Outcome=PD (YES/NO), n=42 cases+22 controls are shown above in Table 4.

Figure 8:
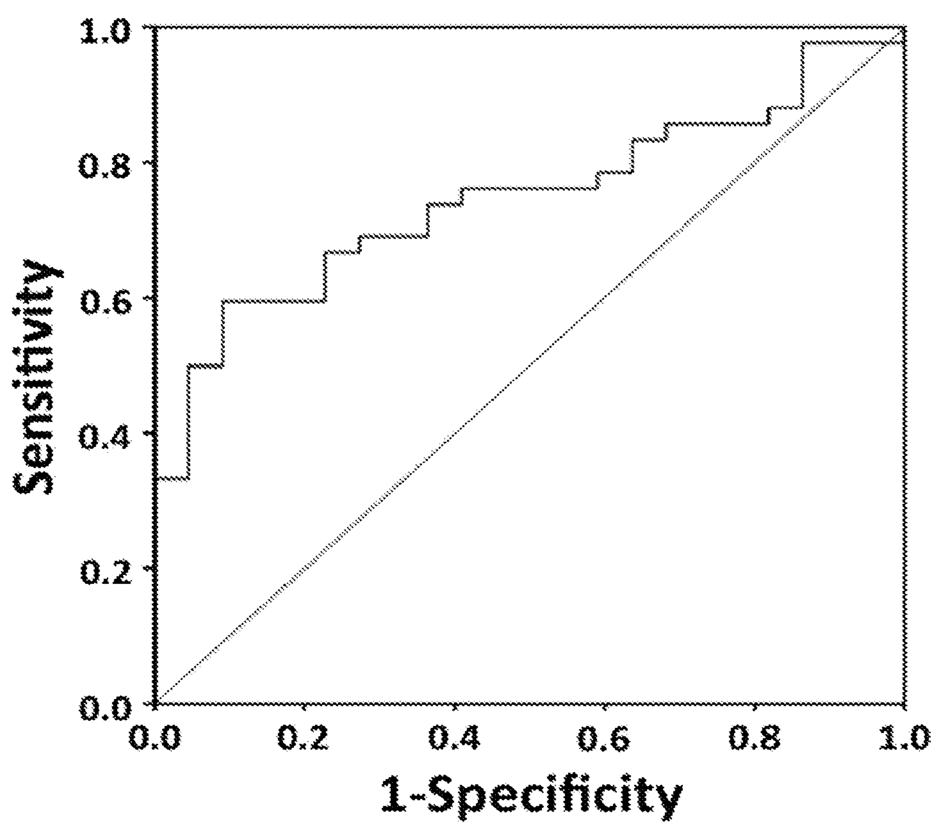
FIG. 8 is a ROC analysis based on predicted probabilities from the model and compared to true disease status.

ROC analysis based on predicted probabilities from the model showing strong discriminating ability are depicted in FIG. 8. The area under the curve of FIG. 8 is provided in Table 4 above.

Example 10: Analyses of Hsa-miR-3613-3p and Hsa-miR-6865-5p in a Cohort of 64 Individuals (22 Control and 42 PD Serum Samples)

Following the protocol of Example 3 it was determined that combinations of hsa-miR-3613-3p and hsa-miR-6865-5p also show high predictability for PD diagnosis. The results of the model with hsa-miR-3613-3p and hsa-miR-6865-5p, Outcome=PD (YES/NO), n=42 cases+22 controls are shown above in Table 4.

Figure 9:
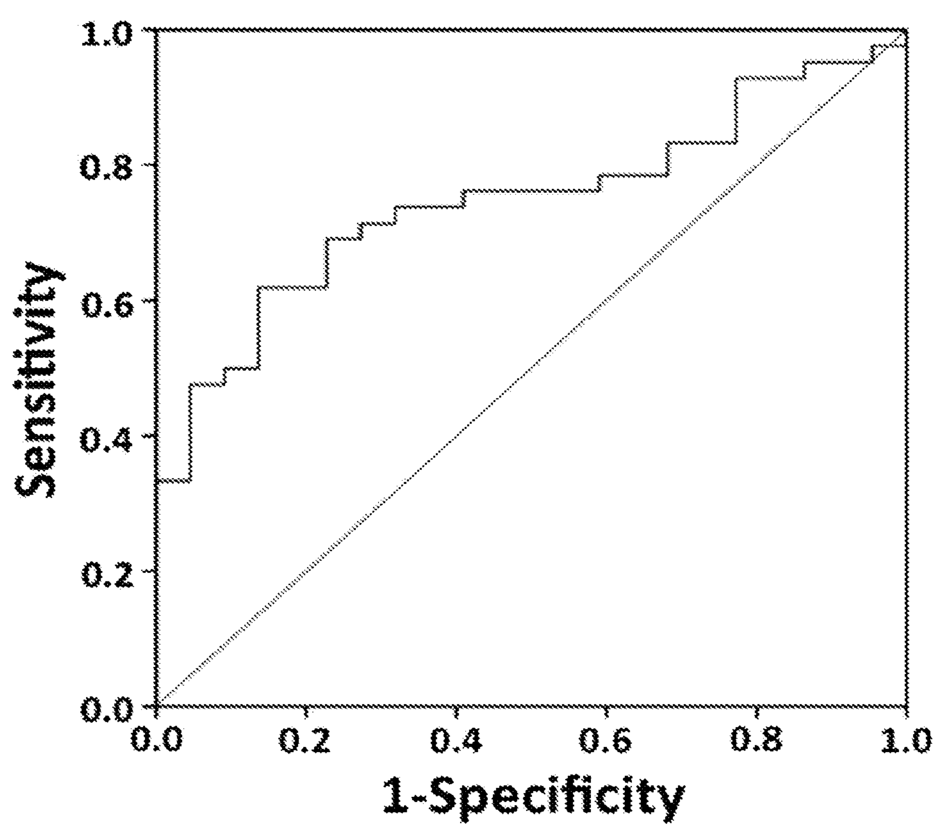
FIG. 9 is a ROC analysis based on predicted probabilities from the model and compared to true disease status.

ROC analysis based on predicted probabilities from the model showing strong discriminating ability are depicted in FIG. 9. The area under the curve of FIG. 9 is provided in Table 4 above.

Example 11: Analyses of Hsa-miR-335-5p, Hsa-miR-3613-3p and Hsa-miR-6865-5p in a Cohort of 64 Individuals (22 Control and 42 PD Serum Samples)

Following the protocol of Example 3 it was determined that combinations of hsa-miR-hsa-miR-335-5p, hsa-miR-3613-3p and hsa-miR-6865-5p also show high predictability for PD diagnosis. The results of the model with hsa-miR-335-5p, hsa-miR-3613-3p and hsa-miR-6865-5p, Outcome=PD (YES/NO), n=42 cases+22 controls are shown above in Table 4.

Figure 10:
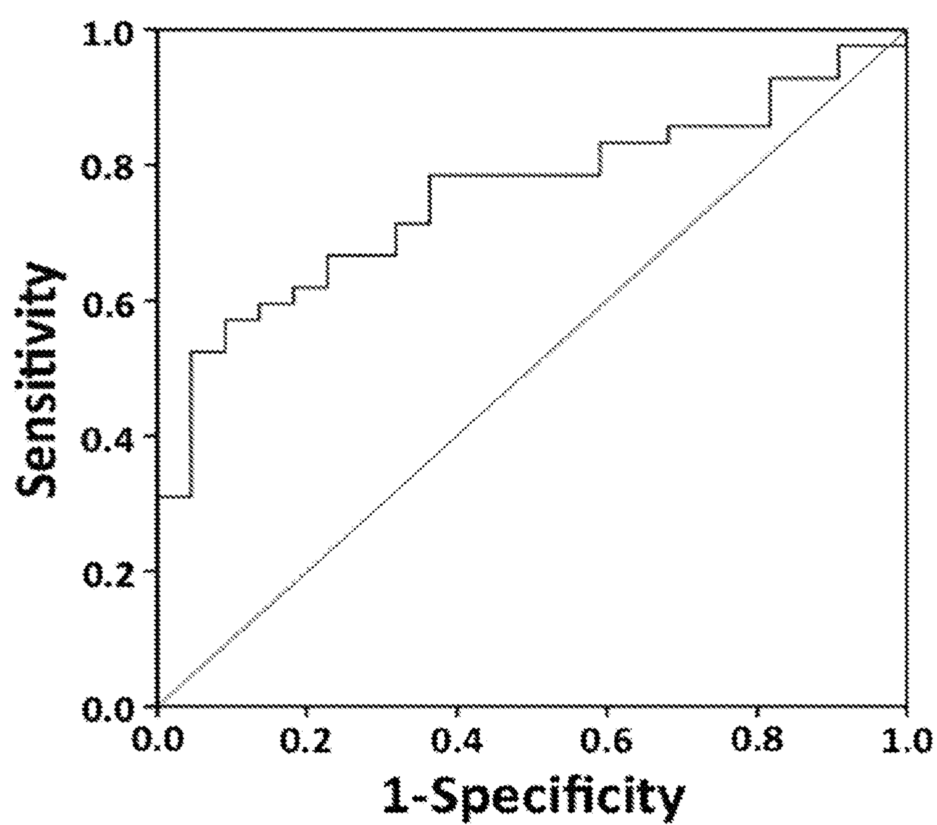
FIG. 10 is a ROC analysis based on predicted probabilities from the model and compared to true disease status.

ROC analysis based on predicted probabilities from the model showing strong discriminating ability are depicted in FIG. 10. The area under the curve of FIG. 10 is provided in Table 4 above.

From the foregoing Example 10 it is evidenced that any combination of three or more microRNAs from the list of 85 identified miRNAs can be used to diagnose the occurrence of PD in patients.

Example 12

Figure 6A:
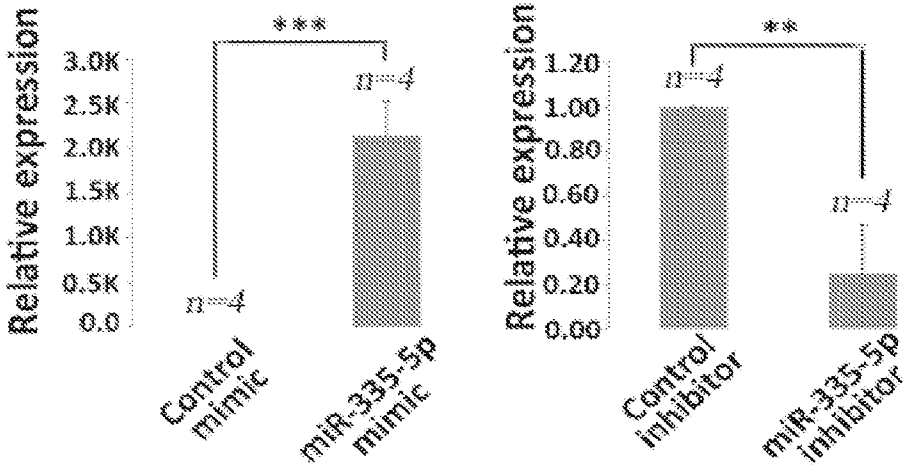
FIG. 6(A)-(H) illustrate microRNAs targeting Parkinson's Disease proteins.
Figure 6B:
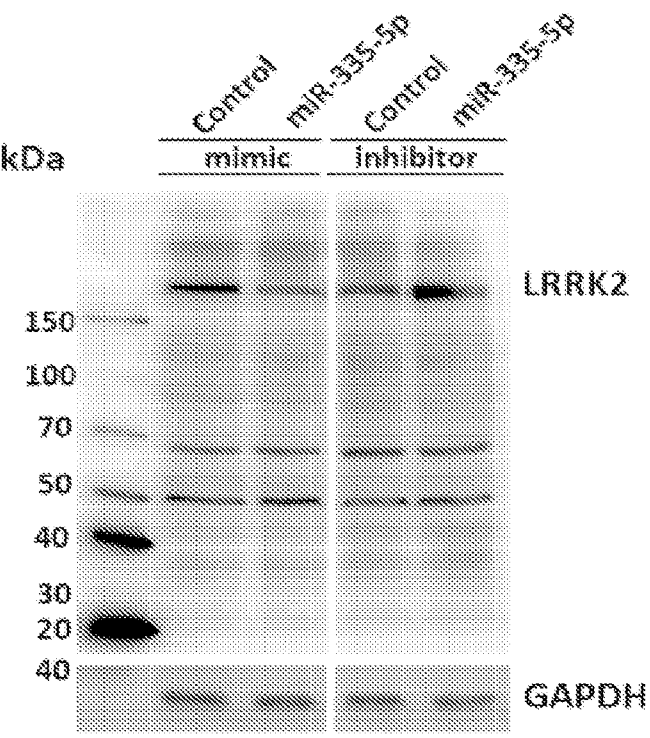
Figure 6C:
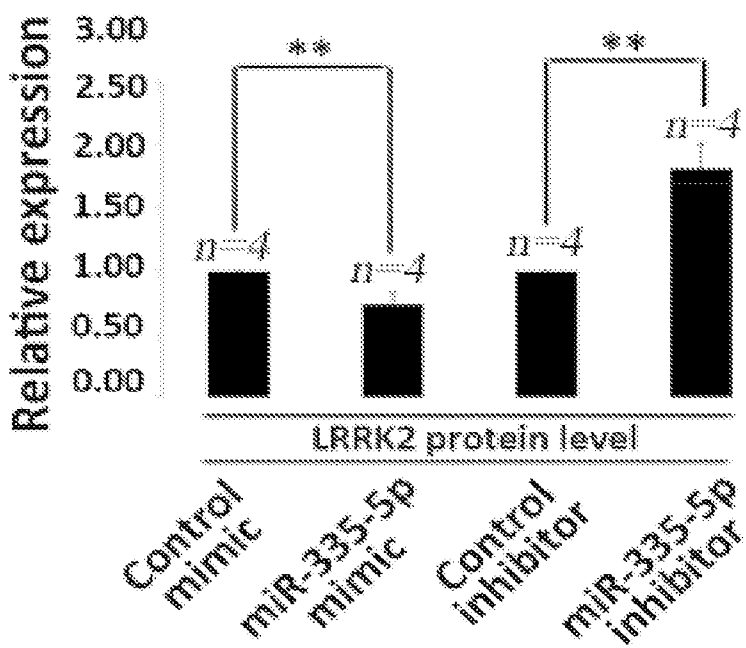
Figure 6D:
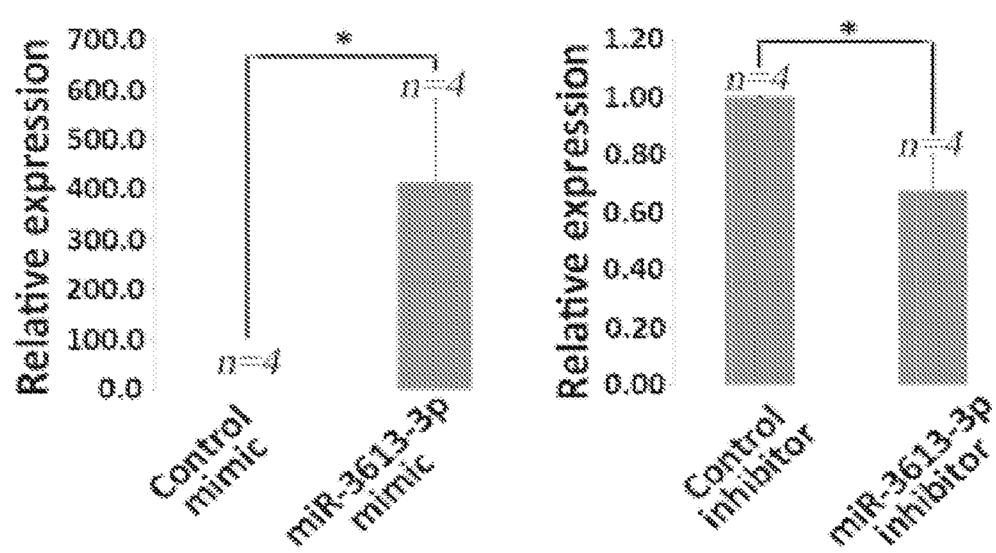
Figure 6E:
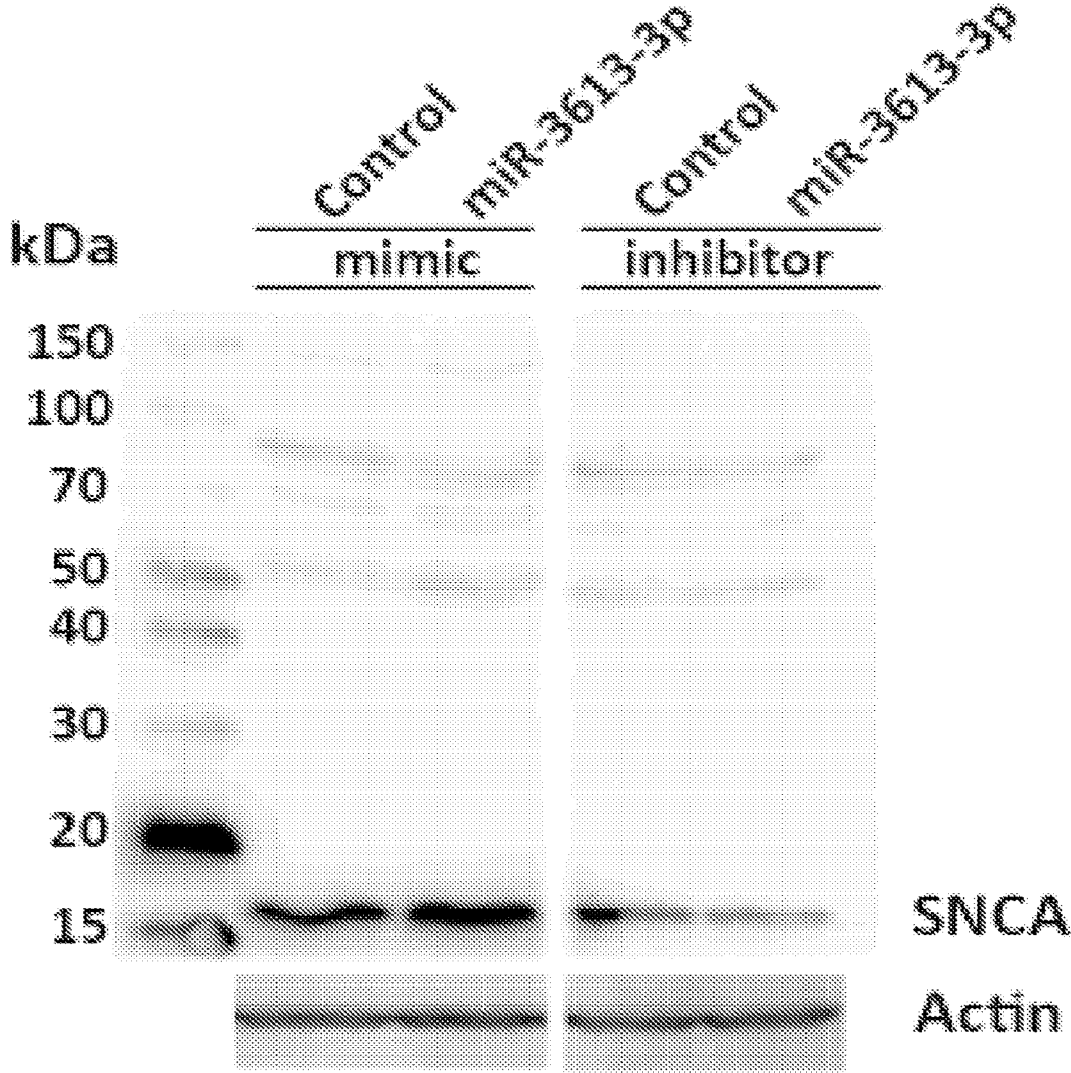
Figure 6F:
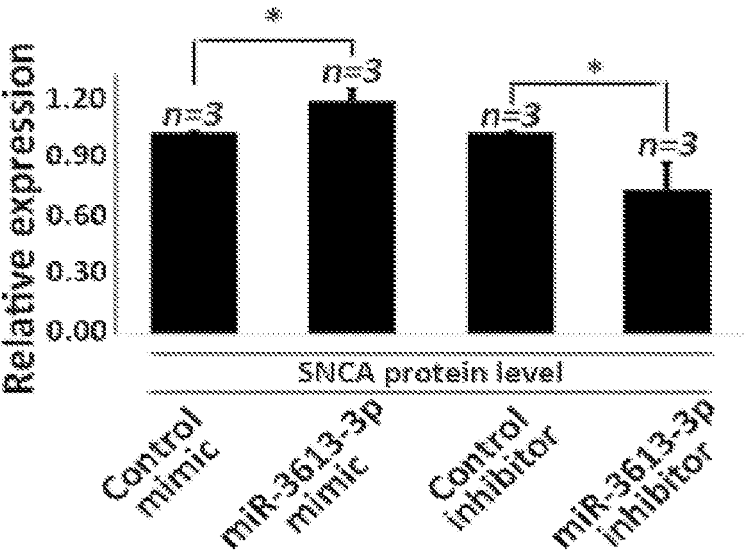
Figure 6G:
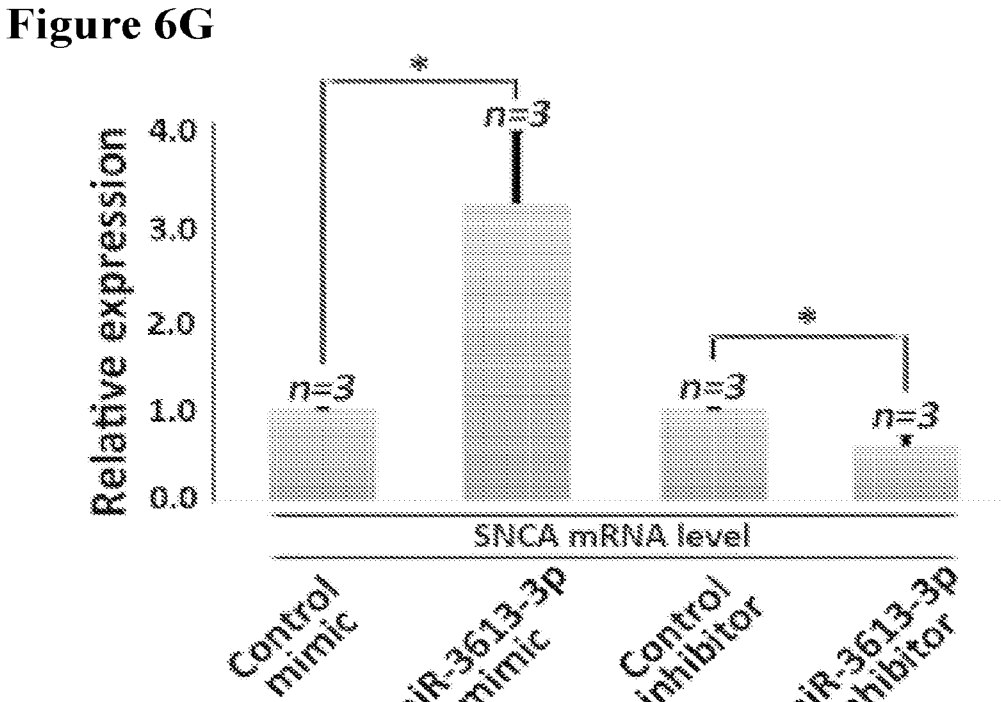
Figure 6H:
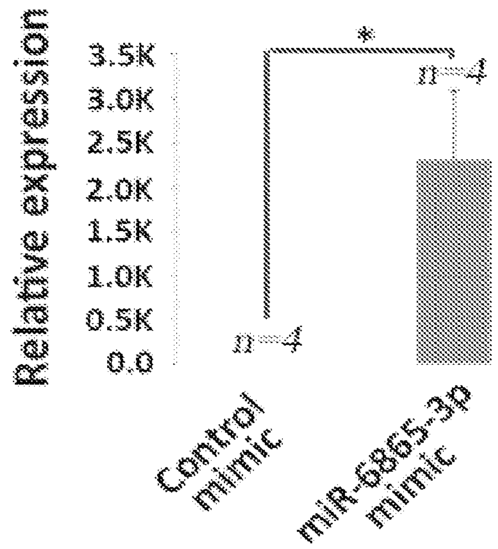
Figure 6H:
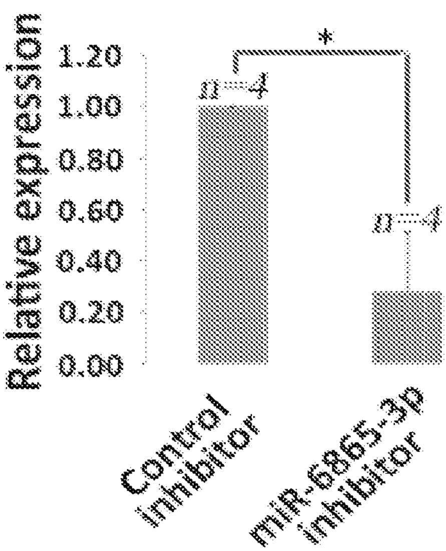

Analysis of hsa-miR-335-5p, hsa-miR-3613-3p and hsa-miR-6865-3p targets using multiple bioinformatics tools show that among others, LRRK2 and Parkin are predicted targets of hsa-miR-335-5p, and SNCA is a predicted target of hsa-miR-3613-3p. The regulation of LRRK2 expression in SHSY-5Y cells as a result of modulation in hsa-miR-335-5p levels was confirmed by western blot analysis. hsa-miR-335-5p was overexpressed (FIG. 6A) and inhibited (FIG. 6A) using mimic and antagomir of hsa-miR-335-5p transfected into neuroblastoma cells. The cells were lysed after 48 hours post-transfection and used for western blot analysis. hsa-miR-335-5p mimic showed downregulation of LRRK2 and hsa-miR-335-5p antagomir showed upregulation of LRRK2 (FIG. 6B, C). The hsa-miR-3613-3p regulated SNCA expression in SH-SY5Y cells in moderation. A similar experimental approach like hsa-miR-335-5p was adopted for hsa-miR-3613-3p (FIG. 6D) and the results showed moderate SNCA upregulation with hsa-miR-3613-3p mimic and a moderate SNCA downregulation with hsa-miR-3613-3p antagomir at protein level (FIG. 6E, F) and transcript level (FIG. 6G).

The target discovery using LC-MS was performed to find novel targets for hsa-miR-335-5p, hsa-miR-3613-3p and hsa-miR-6865-3p.

a. The proteins with differential expression pattern as a result of hsa-miR-335-5p modulation include acadsb, slc4a7, lnp/kiaa1715, supt5h, sdhd. Wdr1, cmpk1, slc25a1, hmgcs1, twf2, ppplr18, exoc8, tm9sf4, kif16b, dnajc2, se1l1, hectd1, gmppb.

b. The proteins with differential expression pattern as a result of hsa-miR-3613-3p modulation include wdr1, gmppb, hmbs, eml4, hebp1, apmap/c20orf3, sord, pcyt2, stat3, top2a, skiv212, cdc20, myo1e, ttl112, atad2, carm1, arfgap1, ppp4r1, nde1/ndel1.

c. The proteins with differential expression pattern as a result of hsa-miR-6865-3p modulation include wdr1, ppplr18, ppp4r1, ube2h, ube3c, stx16, ube4h, gtf2f1, map1b, ube2a, dusp3, arhgap1, nsun2, acox1, fkbp10, fam107b, pofut1, tomm22, hspb8, sbds.

Example 13

Measurement of levels of a combination of two or more miRNAs in serum from patients can assist in distinctly differentiating between a potential PD patient and a healthy individual. A serum sample is obtained from blood withdrawn from patients suspected of PD. The serum is used for total microRNA isolation and enrichment. This RNA would then be tested using qPCR to measure the levels of any two or more of the 85 miRNAs mentioned in Example 1, or any one of three miRNAs mentioned in Examples 5-7. Detectable levels of any two or more of the 85 miRNAs or any one of the three miRNAs confirms the patient has PD. If desired, other sample fluids may be utilized, including plasma, venous or arterial blood, or CSF samples withdrawn by lumbar puncture. Such plasma, blood or CSF samples are processed as above. It will be understood that measurement of more than two miRNAs in combination or a set of combinations used in a test matrix may desirably increase the accuracy of PD diagnosis.

Example 14

Since a combination of miRNA can be used for diagnosis it may be advisable to test all the candidates to eliminate any cohort-based variation. It is understood that any detectable amounts of relevant miRNA will indicate PD pathology. However, those of ordinary skill in the art recognize it may be clinically helpful to use values of 164 v 182 samples to set an artificial threshold for diagnosis. Differential miRNA levels can be used to develop diagnostic biomarker kits that can be used by clinicians in diagnosis as well as in clinical trials. In this study the presence and quantification of miRNA from serum was determined by qRT-PCR which amplifies and quantifies the RNA is question. Other suitable techniques known to those of ordinary skill herein may be alternatively utilized, including use of labeled antisense sequences and labeled antibodies. Suitable antibodies are preferentially selective, referring to a binding reaction between two molecules that is typically more than 10 to 100 times background molecular associations under measurement conditions. Thus, under designated immunoassay conditions, the specified antibodies bind to a particular miRNA sequence, thereby identifying its presence. Specific binding to an antibody under such conditions requires an antibody that is selected for its specificity for a particular miRNA. For example, antibodies raised against a particular miRNA can be selected by subtracting out antibodies that cross-react with other molecules. A variety of immunoassay formats may be used to select antibodies specifically immunoreactive with a particular miRNA including solid-phase ELISA immunoassays (see, e.g., Harlow & Lane, Antibodies, A Laboratory Manual (1988) for a description of immunoassay formats and conditions that can be used to determine specific immunoreactivity). Methods for determining whether two molecules specifically interact are disclosed therein, and methods of determining binding affinity and specificity are well known in the art (see, for example, Harlow and Lane, Antibodies: A laboratory manual (Cold Spring Harbor Laboratory Press, 1988); Friefelder, "Physical Biochemistry: Applications to biochemistry and molecular biology" (W.H. Freeman and Co. 1976)). The term "antibody" as used herein encompasses naturally occurring antibodies as well as non-naturally occurring antibodies, including, for example, single chain antibodies, chimeric, bifunctional and humanized antibodies, as well as antigen-binding fragments thereof, (e.g., Fab', F(ab') 2, Fab, Fv and rIgG). See also, Pierce Catalog and Handbook, 1994-1995 (Pierce Chemical Co., Rockford, IL). See also, e.g., Kuby, J., Immunology, 3rd Ed., W.H. Freeman & Co., New York (1998). Such non-naturally occurring antibodies can be constructed using solid phase peptide synthesis, can be produced recombinantly or can be obtained, for example, by screening combinatorial libraries consisting of variable heavy chains and variable light chains as described by Huse et al., Science, Vol. 246 (1989) 1275-81. These and other methods of making, for example, chimeric, humanized, CDR-grafted, single chain, and bifunctional antibodies are well known to those skilled in the art (Winter and Harris, Immunol. Today, Vol. 14 (1993) 243-46; Ward et al., Nature, Vol. 341 (1989) 544-46; Harlow and Lane, supra, 1988; Hilyard et al., Protein Engineering: A practical approach (IRL Press 1992); Borrabeck, Antibody Engineering, 2d ed. (Oxford University Press 1995). Methods for producing both monoclonal and polyclonal antibodies from identified RNA sequences are well known in the art.

Example 15

Many neurodegenerative diseases are closely related to each other when it comes to symptoms as well as pathological markers. The circulating diagnostic markers for one neurodegenerative disease can be useful for diagnosis of other disease. A method to diagnose other neurodegenerative diseases like Dementia with Lewy body (DLB), Amyotrophic lateral sclerosis (ALS), Alzheimer's disease (AD), Multiple system atrophy (MSA), CorticoBasal Degeneration (CBD), Progressive Supranuclear Palsy (PSP) can also be developed using similar miRNA measurements of candidates mentioned above. Disease specific kits can be developed similar to those mentioned above with various combinations of miRNAs taught herein.

Example 16

The miRNAs detected in one or more combinations can regulate several proteins in the cells. Novel protein targets for PD can be discovered using these microRNAs and their combinations. The involvement of these proteins in PD etiology can be further established to target them for therapy.

Example 17

We have experimentally confirmed the predicted regulation of LRRK2 by hsa-miR-335-5p and SNCA by hsa-miR-3613-3p in dopaminergic neuronal cell lines. Therapeutic intervention to regulate the novel targets mentioned can be achieved by RNA interference technologies.

Example 18

Small nucleic acid molecules derived from miRNAs mentioned above will be designed to therapeutically intervene by specifically targeting genes in PD brains to achieve complete or partial remedy. The effects shown hereinabove will be achieved for precise targeting in brain cells.

What is claimed is:

1. A method, comprising the steps of:

obtaining a sample of a kind selected from the group consisting of whole blood, plasma and serum from a human patient;

determining a differential level of at least three miRNAs selected from the group consisting of SEQ ID NOS: 3-86 within said sample compared to a differential level in a sample of the same kind from a healthy control;

correlating differential levels of at least 1.2 fold above that of the healthy control for said miRNAs to a disease state of Parkinson's disease in said human patient; and administering treatment for Parkinson's disease to said human patient, wherein said treatment comprises administering L-dopa, peripheral decarboxylase inhibitor, dopamine agonist, catechol-O-methyltransferase inhibitor, amantadine or a monoamine oxidase B inhibitor to said human patient.

2. The method according to claim 1, wherein the differential level of said miRNAs is determined using qRT-PCR.

3. The method according to claim 1, wherein the differential level of said miRNAs is determined using labeled antisense nucleotide sequences.

4. A method, comprising the steps of:

obtaining a sample of a kind selected from the group consisting of whole blood, plasma and serum from a human patient;

determining a differential level of at least two miRNAs selected from the group consisting of SEQ ID NOS: 3, 5, 6, 7, 8, 9, 10, 11, 12, 13, 14, 15, 16, 22, 24, 25, 27, 28, 31, 30, 32, 33, 37, 38, 40, 42, 43, 44, 46, 47, 48, 49, 50, 51, 55, 56, 57, 58, 59, 60, 62, 63, 64, 67, 68, 71, 72, 74, 75, 77, 78, 80, 81, 85 and 86 within said sample compared to a differential level in a sample of the same kind from a healthy control;

correlating differential levels of at least 1.2 fold above that of the healthy control for said miRNAs to a disease state of Parkinson's disease in said human patient; and administering treatment for Parkinson's disease to said human patient, wherein said treatment comprises administering L-dopa, peripheral decarboxylase inhibitor, dopamine agonist, catechol-O-methyltransferase inhibitor, amantadine or a monoamine oxidase B inhibitor to said human patient.

5. The method according to claim 4, wherein the differential level of said miRNAs is determined using qRT-PCR.

6. The method according to claim 4, wherein the differential level of said miRNAs is determined using labeled antisense nucleotide sequences.

7. A method, comprising the steps of:

obtaining a sample of a kind selected from the group consisting of whole blood, plasma and serum from a human patient;

determining a differential level of at least two miRNAs selected from the group consisting of SEQ ID NOS: 4, 17, 18, 19, 20, 21, 23, 26, 29, 34, 35, 36, 39, 45, 52, 53, 54, 61, 65, 66, 69, 70, 73, 76, 79, 82, 83 and 84 within said sample compared to a differential level in a sample of the same kind from a healthy control;

correlating differential levels of at least 1.2 fold above that of the healthy control for said miRNAs to a disease state of Parkinson's disease in said human patient; and administering treatment for Parkinson's disease to said human patient, wherein said treatment comprises administering L-dopa, peripheral decarboxylase inhibitor, dopamine agonist, catechol-O-methyltransferase inhibitor, amantadine or a monoamine oxidase B inhibitor to said human patient.

8. The method according to claim 7, wherein the differential level of said miRNAs is determined using qRT-PCR.

9. The method according to claim 7, wherein the differential level of said miRNAs is determined using labeled antisense nucleotide sequences.

10. A method, comprising the steps of:

obtaining a sample of a kind selected from the group consisting of whole blood, plasma and serum from a human patient;

determining a differential level of at least one miRNA selected from the group consisting of SEQ ID NOS: 15, 22, 24, 25, 52, 54, 55 and 77 within said sample compared to a differential level in a sample of the same kind from a healthy control;

correlating differential levels of at least 1.2 fold above that of the healthy control for said miRNAs to a disease state of Parkinson's disease in said human patient; and administering treatment for Parkinson's disease to said human patient, wherein said treatment comprises administering L-dopa, peripheral decarboxylase inhibitor, dopamine agonist, catechol-O-methyltransferase inhibitor, amantadine or a monoamine oxidase B inhibitor to said human patient.

11. The method according to claim 10, comprising determining the differential level of at least two miRNAs selected from the group consisting of SEQ ID NOS: 15, 21, 22, 24, 25, 52, 54, 55 and 77 within said sample.

12. The method according to claim 10, comprising determining the differential level of at least two miRNAs selected from the group consisting of SEQ ID NOS: 22, 25 and 77 within said sample.

13. The method according to claim 11, wherein said at least two miRNAs comprise SEQ ID NOS: 22 and 25.

14. The method according to claim 11, wherein said at least two miRNAs comprise SEQ ID NOS: 22 and 77.

15. The method according to claim 11, wherein said at least two miRNAs comprise SEQ ID NOS: 25 and 77.

16. The method according to claim 10, comprising determining the differential level of each of SEQ ID NOS: 22, 25 and 77 within said sample.

17. The method according to claim 11, wherein said at least two miRNAs comprise SEQ ID NOS: 15 and 22.

18. The method according to claim 11, wherein said at least two miRNAs comprise SEQ ID NOS: 21 and 22.

19. The method according to claim 11, wherein said at least two miRNAs comprise SEQ ID NOS: 22 and 24.

20. The method according to claim 11, wherein said at least two miRNAs comprise SEQ ID NOS: 22 and 52.

21. The method according to claim 11, wherein said at least two miRNAs comprise SEQ ID NOS: 22 and 54.

22. The method according to claim 11, wherein said at least two miRNAs comprise SEQ ID NOS: 22 and 55.

23. The method according to claim 11, wherein said at least two miRNAs comprise SEQ ID NOS: 15 and 25.

24. The method according to claim 11, wherein said at least two miRNAs comprise SEQ ID NOS: 21 and 25.

25. The method according to claim 11, wherein said at least two miRNAs comprise SEQ ID NOS: 24 and 25.

26. The method according to claim 11, wherein said at least two miRNAs comprise SEQ ID NOS: 25 and 52.

27. The method according to claim 11, wherein said at least two miRNAs comprise SEQ ID NOS: 25 and 54.

28. The method according to claim 11, wherein said at least two miRNAs comprise SEQ ID NOS: 25 and 55.

29. The method according to claim 11, wherein said at least two miRNAs comprise SEQ ID NOS: 15 and 77.

30. The method according to claim 11, wherein said at least two miRNAs comprise SEQ ID NOS: 21 and 77.

31. The method according to claim 11, wherein said at least two miRNAs comprise SEQ ID NOS: 24 and 77.

32. The method according to claim 11, wherein said at least two miRNAs comprise SEQ ID NOS: 52 and 77.

33. The method according to claim 11, wherein said at least two miRNAs comprise SEQ ID NOS: 54 and 77.

34. The method according to claim 11, wherein said at least two miRNAs comprise SEQ ID NOS: 55 and 77.

* * * * *